(12) United States Patent
Cress et al.

(10) Patent No.: US 12,263,147 B2
(45) Date of Patent: Apr. 1, 2025

(54) TREATMENT OF STK11-LOSS CANCERS

(71) Applicant: H. Lee Moffitt Cancer Center and Research Institute, Inc., Tampa, FL (US)

(72) Inventors: Douglas W. Cress, Wesley Chapel, FL (US); John Cleveland, Land O'Lakes, FL (US); Nicholas Gimbrone, Atlanta, GA (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 533 days.

(21) Appl. No.: 17/298,251

(22) PCT Filed: Dec. 26, 2019

(86) PCT No.: PCT/US2019/068571
§ 371 (c)(1),
(2) Date: May 28, 2021

(87) PCT Pub. No.: WO2020/139941
PCT Pub. Date: Jul. 2, 2020

(65) Prior Publication Data
US 2022/0110898 A1 Apr. 14, 2022

Related U.S. Application Data

(60) Provisional application No. 62/830,795, filed on Apr. 8, 2019, provisional application No. 62/785,468, filed on Dec. 27, 2018.

(51) Int. Cl.
*A61K 31/198* (2006.01)
*A61K 45/06* (2006.01)
*A61P 35/00* (2006.01)

(52) U.S. Cl.
CPC ............ *A61K 31/198* (2013.01); *A61K 45/06* (2013.01); *A61P 35/00* (2018.01)

(58) Field of Classification Search
CPC ........ A61K 31/198; A61K 45/06; A61P 35/00
See application file for complete search history.

(56) References Cited

U.S. PATENT DOCUMENTS

| | | | | |
|---|---|---|---|---|
| 2002/0045663 A1* | 4/2002 | Levenson | ............... | A61P 43/00 514/564 |
| 2003/0203956 A1* | 10/2003 | Masterrer | ............... | A61K 31/42 514/565 |
| 2016/0193239 A1* | 7/2016 | Baylin | ............... | A61K 39/3955 435/375 |

FOREIGN PATENT DOCUMENTS

| | | | | |
|---|---|---|---|---|
| WO | WO-0069434 A1 | * | 11/2000 | ........... A61K 31/198 |
| WO | WO-2017210624 A1 | * | 12/2017 | ............. A61P 11/00 |

OTHER PUBLICATIONS

Chen et al., "cAMP/CREB-regulated LINC00473 marks LKB1-inactivated lung cancer and mediates tumor growth," J Clin invest 126:2267-2279 (2016) (Year: 2016).*
Carretero et al., "Novel and natural knockout lung cancer cell lines for the LKB1/STK11 tumor suppressor gene," oncogene 23:4037-4040 (2004) (Year: 2004).*
Creaven et al, "Evaluation of alpha-difluoromethylornithine as a potential chemopreventive agent: tolerance to daily oral administration in humans," Cancer Epidemiol Biomarkers Prev 2: 243-247 (1993) (Year: 1993).*
International Search Report issued for PCT/US2019/068571, mailed Mar. 12, 2020.
Luk et al., Successful Treatment with DL-a-Difluoromethylornithine in Established Human Small Cell Variant Lung Carcinoma Implants in Athymic Mice, Cancer Research, vol. 43, p. 4239-4243, 1983.
Avizienyte et al., LKB1 Somatic Mutations in Sporadic Tumors, American Journal of Pathology, vol. 154, No. 3, p. 677-681, 1999.

* cited by examiner

*Primary Examiner* — Julie Ha
*Assistant Examiner* — Kristina M Hellman
(74) *Attorney, Agent, or Firm* — Thomas | Horstemeyer, LLP

(57) ABSTRACT

As disclosed herein, inhibition of the ornithine decarboxylase 1-driven pathway can restore immunotherapeutic efficacy in lung cancer with lost STK11 function. Therefore, disclosed herein are compositions and methods for treating a lung cancer in a subject using an ornithine decarboxylase (ODC) inhibitor, such as difluoromethylornithine. In particular, disclosed is a method for using an ODC inhibitor to sensitize a lung cancer to immunotherapy. The method can involve assaying the subject for STK11 function. The method can also involve treating the subject with an immunotherapy, such as anti-PD-1/PD-L1 immunotherapy.

7 Claims, 26 Drawing Sheets

| Gene Set Name [# Genes (K)] | Description | # Genes in Overlap (k) | k/K | p-value | FDR q-value |
|---|---|---|---|---|---|
| HALLMARK_INFLAMMATORY_RESPONSE (200) | Genes defining inflammatory response. | 12 | | 8.77 e$^{-13}$ | 2.19 e$^{-11}$ |
| HALLMARK_INTERFERON_GAMMA_RESPONSE (200) | Genes up-regulated in response to IFNG [GeneID=3458]. | 12 | | 8.77 e$^{-13}$ | 2.19 e$^{-11}$ |
| HALLMARK_INTERFERON_ALPHA_RESPONSE (97) | Genes up-regulated in response to alpha interferon proteins. | 7 | | 1.58 e$^{-8}$ | 2.63 e$^{-7}$ |
| HALLMARK_ESTROGEN_RESPONSE_LATE (200) | Genes defining late response to estrogen. | 7 | | 2.19 e$^{-6}$ | 2.19 e$^{-5}$ |
| HALLMARK_IL2_STAT5_SIGNALING (200) | Genes up-regulated by STAT5 in response to IL2 stimulation. | 7 | | 2.19 e$^{-6}$ | 2.19 e$^{-5}$ |
| HALLMARK_ALLOGRAFT_REJECTION (200) | Genes up-regulated during transplant rejection. | 6 | | 2.85 e$^{-5}$ | 1.78 e$^{-4}$ |
| HALLMARK_ESTROGEN_RESPONSE_EARLY (200) | Genes defining early response to estrogen. | 6 | | 2.85 e$^{-5}$ | 1.78 e$^{-4}$ |
| HALLMARK_TNFA_SIGNALING_VIA_NFKB (200) | Genes regulated by NF-кB in response to TNF [GeneID=7124]. | 6 | | 2.85 e$^{-5}$ | 1.78 e$^{-4}$ |
| HALLMARK_APICAL_SURFACE (44) | Genes encoding proteins over-represented on the apical surface of epithelial cells, e.g., important for cell polarity (apical area). | 3 | | 2.94 e$^{-4}$ | 1.63 e$^{-3}$ |
| HALLMARK_FATTY_ACID_METABOLISM (158) | Genes encoding proteins involved in metabolism of fatty acids. | 4 | | 1.22 e$^{-3}$ | 5.95 e$^{-3}$ |

FIG. 2F

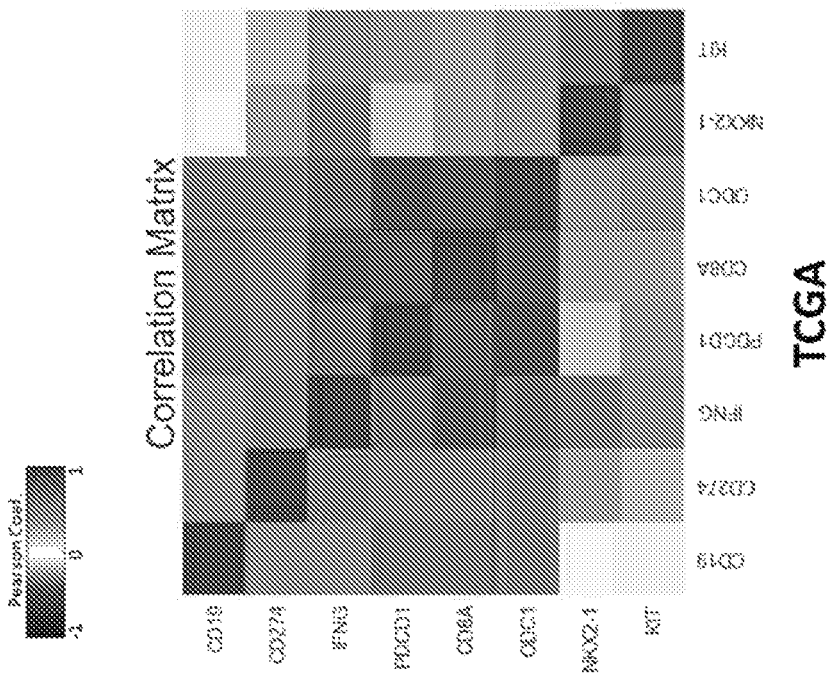
FIG. 4G TCGA
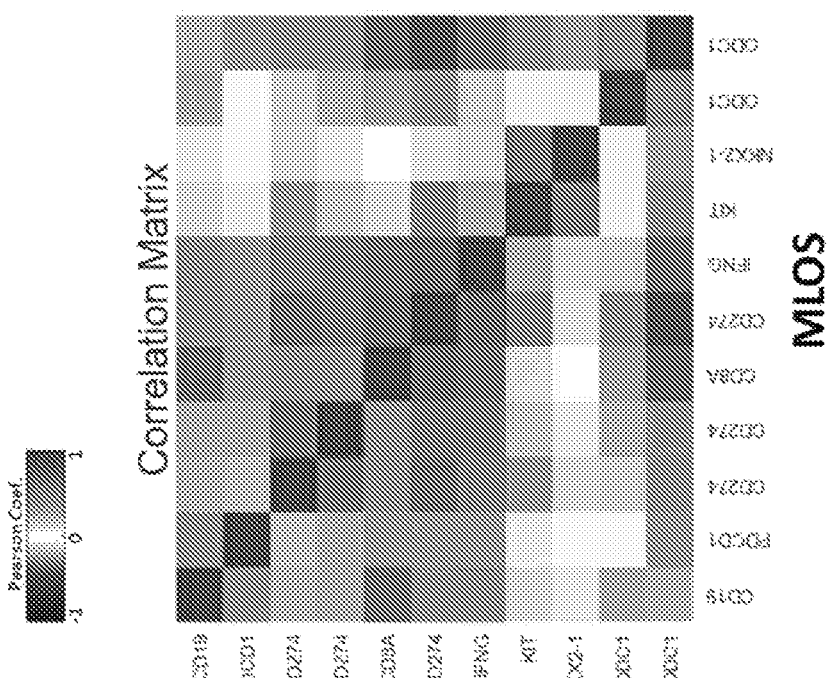
FIG. 4F MLOS

TREATMENT OF STK11-LOSS CANCERS

CROSS-REFERENCE TO RELATED APPLICATIONS

This application is a National Stage of International Application No. PCT/US2019/068571, filed Dec. 26, 2019, which claims benefit of U.S. Provisional Application No. 62/785,468, filed Dec. 27, 2018, and U.S. Provisional Application No. 62/830,795, filed Apr. 8, 2019, which are hereby incorporated herein by reference in their entireties.

BACKGROUND

In the current age of cancer therapeutics, immunotherapy has provided significant strides towards increased progression-free survival and even permanent remission in a small percentage of patients. Some of the best responses to immunotherapy have been seen in subsets of immunogenic cancers such as melanoma and lung cancer. However, despite successful treatments, the response rate rarely exceeds 25% (Qin H, et al. Am J Transl Res 2018 10(8):2234-45; Raju S, et al. Immunotargets Ther 2018 7:63-75). Prediction of the patients who will benefit from immunotherapy through clinical biomarkers is one hurdle to overcome. Perhaps the most difficult challenge is unraveling the mechanisms underlying immunocompromised non-responders (Villanueva N, et al. Ther Adv Respir Dis 2018 12:1753466618794133; Yu Y, et al. Oncol Lett 2018 16(4):4105-13). Increased understanding of these adaptations will pave the way for better personalized combination therapy

SUMMARY

STK11, also known as LKB1, is a well-established mediator of stress and has been shown to be mutated in roughly 18% of all lung adenocarcinomas (LUAD), the most incident histology of all lung cancer (Cancer Genome Atlas Research N. Nature 2014 511(7511):543-50). STK11 lies downstream of PKC (protein kinase C) and upstream of AMPK and is responsible for phosphorylating ~14 kinases in response to alterations in cellular energy homeostasis (Alexander A, et al. FEBS Lett 2011 585(7):952-7; Gan R Y, et al. Int J Mol Sci 2014 15(9):16698-718). In times of metabolic stress, or a high cAMP/ATP ratio, STK11 phosphorylates AMPK resulting in activation of catabolic pathways over anabolic ones. This molecular switch has been displayed by the role of STK11 on mTOR inhibition and autophagy induction. Changes in the functional status of STK11 have been linked to alterations of methylation, metabolism, cellular polarity, differentiation, and apoptosis (Boudeau J, et al. FEBS Lett 2003 546(1):159-65; Lizcano J M, et al. EMBO J 2004 23(4):833-43; Zhou W, et al. Chin J Cancer 2013 32(8):427-33; Parker S J, et al. Metab Eng 2017; Mans L A, et al. Sci Rep 2017 7(1):7327; Tsai L H, et al. Oncogene 2014 33(29):3851-60). More recently, studies have pointed to STK11's role in immune evasion. Patients harboring tumors deficient in STK11 signaling have been shown to have a reduction in the infiltration of cytotoxic T-cells and respond poorly to anti PD-L1 therapy (Skoulidis F, et al. Cancer Discov 2015 5(8):860-77; Schabath M B, et al. Oncogene 2016 35(24):3209-16; Biton J, et al. Clin Cancer Res 2018 24(22):5710-5723; Piton N, et al. Modern Pathol 2018 31:746; Skoulidis F, et al. Cancer Discov 2018 8(7):822-835).

Using gene expression as a classifier, it was determined that over 30% of lung adenocarcinomas are predicted to have lost STK11 function. Multiple gene-set enrichment analyses reveal that those tumors with predicted loss of STK11 upregulate amino acid catabolism, the urea cycle, and polyamine synthesis. ODC1 (ornithine decarboxylase 1), the rate limiting step in polyamine biosynthesis, was identified as one of the strongest biomarkers of STK11 loss. ODC1 over expression in STK11 loss tumors was unique to human samples and not significantly associated with STK11 loss in commonly-used cell line, mouse or patient-derived xenograft models. Untargeted LS-MS metabolomics validate the predictions based on gene/protein expression, demonstrating that tumors with loss of STK11 function have increased production of putrescine, gamma-aminobutyric acid (GABA), and pyridoxal with decreases in ornithine and histamine.

Therefore, as disclosed herein, inhibition of this ODC-driven pathway can restore immunotherapeutic efficacy in an otherwise unresponsive cohort. ODC1 is targetable through the FDA-approved drug DFMO (Difluromethylornithine), which acts as an irreversible inhibitor of ODC1. Until now, DFMO has not been considered a treatment strategy for lung cancer, as it is most commonly associated with MYC/MYCN driven diseases such as prostate cancer or neuroblastoma, respectively.

Therefore, disclosed herein is a method for treating a lung cancer in a subject that involves administering the subject an ornithine decarboxylase (ODC) inhibitor. In some embodiments, the ornithine decarboxylase inhibitor is DFMO. In some embodiments, the ODC inhibitor is N-(4'-Pyridoxyl)-Ornithine(BOC)-OMe [POB]. In some embodiments, the ODC inhibitor is a-methyl ornithine. In some embodiments, the ODC inhibitor is antizyme (AZ), which binds to ODC and accelerates the ATP-dependent degradation of the ODC enzyme, as disclosed in U.S. Pat. No. 6,914,079, which is incorporated herein in its entirety by reference. In some embodiments, the ODC inhibitor is combined with AMXT 1501, an inhibitor of the polyamine transport system.

In particular embodiments, the cancer is a lung cancer with lost STK11 function. Therefore, in some embodiments, the method further involves assaying the subject for STK11 function. For examples, the method can involve assaying a sample from the subject 1) for STK11 somatic mutations, 2) for expression of protein biomarkers (including STK11, ODC1, TTF1 and c-Kit) or 3) for expression of mRNAs biomarkers (as described herein, see Table 3).

The method can further involve treating the subject with an immunotherapy, such as anti-PD-1/PD-L1 immunotherapy. Therefore, also disclosed is a composition comprising an ODC inhibitor and an anti-PD-1/PD-L1 agent.

The disclosed methods are relevant to any immunogenic cancers, such as melanoma and lung cancers, tumor that can have lost STK11 function.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a Cbioportal bargraph representing the detectable STK11 mutation frequency amongst all cancer types, with the most frequent histology being large cell neuroendocrine cancers followed by lung adenocarcinoma. FIG. 1B is an introduction of the cohorts we will be using for the duration of the study. Moffitt's Lung Overall Survival (MLOS) cohort contains 442 patients, with 150 of those patients on a tumor microarray for IHC staining, and 126 of those patients were analyzed using LC-MS untargeted metabolomics. TOGA contains 515 LUAD tumor samples with 360 of those patients having reverse phase protein array (RPPA) data. These two cohorts will be used in parallel to confirm our hypotheses. FIG. 1C is a Venn-Diagram displaying the overlap of genes changing as a result of STK11 DNA level mutations in both cohorts. Using a Bonferroni corrected p-value of <1e-10 and a linear fold change of +/−1.5, 29 genes were found to be significantly altered in both studies. FIG. 1D shows gene set enrichment utilizing both Genemania and mSigDB's Hallmark datasets suggest disruption of the canonical polyamine metabolism pathway highlighted here.

FIGS. 2A to 2H shows generation of a gene expression signature to predict STK11 loss of function in patients. FIG. 2A-2B show principal component analysis using the 29 genes from FIG. 1C in the MLOS (FIG. 2A) and TOGA (FIG. 2B) cohorts. Patients with detected DNA mutations in STK11 are indicated in blue and wildtype in red. FIG. 2C-2D are volcano plots of genes changing between patients with a signature score >0 (mutant) or <0 (wildtype) in MLOS (FIG. 2C) and TOGA (FIG. 2D). X axis is the log 2 fold change and Y axis is the −log 10 of the students t-test p-value. FIG. 2E is a Venn-Diagram displaying genes changing by a Bonferroni corrected p-value of <1e-15 and a linear fold change of +/−1.5. In both TOGA and MLOS there are now 137 genes that overlap. FIG. 2F shows MsigDB's Hallmark geneset overlap between the 137 genes seen in FIG. 2E. FIG. 2G shows a method of gene set enrichment using unsupervised K-means clustering of genesets between patients with predicted STK11 loss of function. FIG. 2H shows application of the STK11 signature to TCGA's pan-cancer dataset by cancer type.

FIG. 3A is a Boxplot of predicted STK11 mutant (COLE n=24, GSE68950 n=14) and WT(CCLE n=50, GSE68950 n=24) cells for ODC1. FIG. 3B is a Boxplot of ODC1 expression in primary lung tumors from KRAS (n=9) and STK11/KRAS (n=9) transgenic mice in GSE21581. FIG. 3C is a Boxplot of ODC1 expression in human patient derived xenograft models from GSE78806 based on predicted STK11 status. FIG. 3D is a Boxplot of ODC1 expression between patients with predicted STK11 loss of function and wildtype in MLOS (left) and TOGA (right). FIG. 3E is a Western blot on patient samples based on DNA level detected mutations.

FIGS. 4A to 4G shows STK11 loss of function and polyamine metabolism is associated with lack of immune infiltration (FIGS. 4A, 4C) K-means clustering was used on mSigDB's Interferon Geneset (n=159 genes) to cluster patients from MLOS (FIG. 4A top) and TOGA (FIG. 4C top) into 3 subsets of varying interferon response. Corresponding DNA Mutation rate was calculated by Fishers Exact test between subsets (FIGS. 4A, 4C bottom).

FIGS. 4B and 4D show the STK11 signature calculated in these three subsets in MLOS (FIG. 4B) and TOGA (FIG. 4D). FIG. 4E shows CD274 (PD-L1) expression was determined in TOGA (far left) MLOS (far right) and paired with RPPA data in TOGA (middle). FIGS. 4F and 4G show Pearson correlation coefficient plotted between canonical immune markers (CD19, CD274, IFNG, PDCD1, CD8A) and STK11 related biomarkers (ODC1,NKX2-1,KIT) in MLOS (FIG. 4F) and TOGA (FIG. 4G).

FIG. 5A is a Volcano plot of average peak heights of metabolites in STK11 mutants compared to wildtype. FIG. 5B is a correlation matrix displaying Pearson correlation coefficient between metabolites significantly altered in STK11 mutants. FIG. 5C shows plotted correlation between ODC1 gene expression and linear peak height of Putrescine.

FIG. 5D is a schematic representing the potential mechanism by which STK11 mutants alter the GABA-Putrescine metabolic pathway.

FIG. 7A shows objective response rate (RECISTv1.1) to PD-1/PD-L1 inhibitors in STK11/LKB1-mutant and wild-type patients with PD-L1-positive nonsquamous NSCLC (≥1%) from MDACC (n=66). PD-L1 expression was assessed using the FDA-approved 22C3 pharmDx assay (Dako). A two-tailed Fisher exact test (computed from a 2×2 contingency table) was used to assess the significance of the association between group membership (STK11/LKB1-mutant versus STK11/LKB1-wild-type) and best overall response (PR/CR vs. SD/PD). FIG. 7B shows fractions of PD-L1 low-positive (1%-49%) and PD-L1 high-positive (≥50%) tumors in the STK11/LKB1-mutant and wild-type groups. FIG. 7C shows Kaplan-Meier estimates of progression-free survival with PD-1/PD-L1 blockade in STK11/LKB1-mutant and wild-type groups. Tick marks represent data censored at the last time the patient was known to be alive and without disease progression (date of last radiologic assessment). FIG. 7D shows Kaplan-Meier estimates of overall survival with PD-1 inhibitors in the STK11/LKB1-mutant and wild-type groups. Tick marks represent data censored at the last time the patient was known to be alive.

DETAILED DESCRIPTION

Figure 1A:
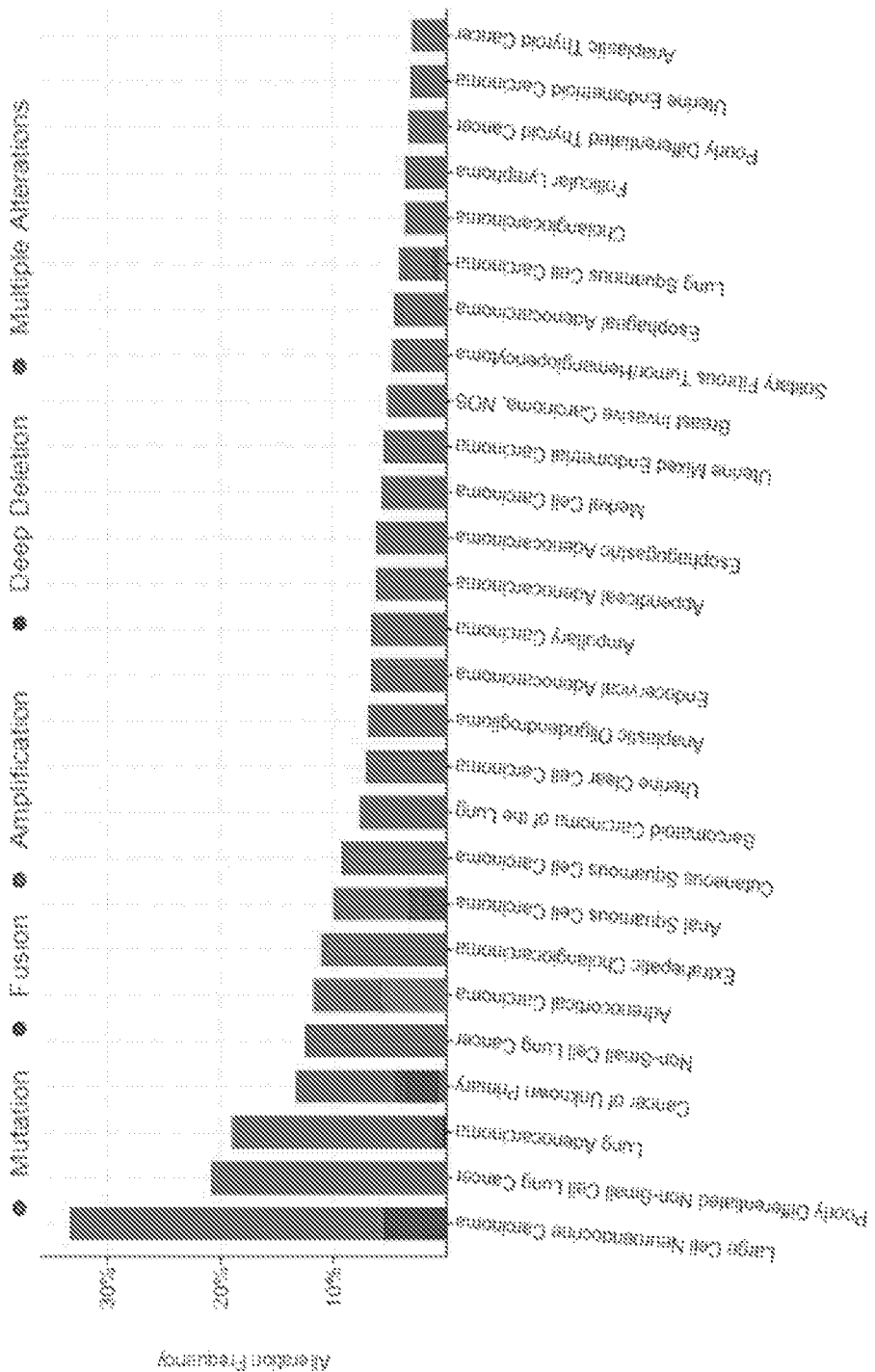
FIGS. 1A to 1D show STK11 mutations result in transcriptional changes related to amino acid metabolism.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

The term "sample from a subject" refers to a tissue (e.g., tissue biopsy), organ, cell (including a cell maintained in culture), cell lysate (or lysate fraction), biomolecule derived from a cell or cellular material (e.g. a polypeptide or nucleic acid), or body fluid from a subject. Non-limiting examples of body fluids include blood, urine, plasma, serum, tears, lymph, bile, cerebrospinal fluid, interstitial fluid, aqueous or vitreous humor, colostrum, sputum, amniotic fluid, saliva, anal and vaginal secretions, perspiration, semen, transudate, exudate, and synovial fluid.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "sample from a subject" refers to a tissue (e.g., tissue biopsy), organ, cell (including a cell maintained in culture), cell lysate (or lysate fraction), biomolecule derived from a cell or cellular material (e.g. a polypeptide or nucleic acid), or body fluid from a subject. Non-limiting examples of body fluids include blood, urine, plasma, serum, tears, lymph, bile, cerebrospinal fluid, interstitial fluid, aqueous or vitreous humor, colostrum, sputum, amniotic fluid, saliva, anal and vaginal secretions, perspiration, semen, transudate, exudate, and synovial fluid.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

Disclosed herein are compositions and method for sensitizing a lung cancer in a subject to immunotherapy involves administering to the subject an ornithine decarboxylase (ODC) inhibitor.

In some embodiments, the immunotherapy involves a checkpoint inhibitor. The two known inhibitory checkpoint pathways involve signaling through the cytotoxic T-lymphocyte antigen-4 (CTLA-4) and programmed-death 1 (PD-1) receptors. These proteins are members of the CD28-B7 family of cosignaling molecules that play important roles throughout all stages of T cell function. The PD-1 receptor (also known as CD279) is expressed on the surface of activated T cells. Its ligands, PD-L1 (B7-H1; CD274) and PD-L2 (B7-DC; CD273), are expressed on the surface of APCs such as dendritic cells or macrophages. PD-L1 is the predominant ligand, while PD-L2 has a much more restricted expression pattern. When the ligands bind to PD-1, an inhibitory signal is transmitted into the T cell, which reduces cytokine production and suppresses T-cell proliferation. Checkpoint inhibitors include, but are not limited to antibodies that block PD-1 (Nivolumab (BMS-936558 or MDX1106), CT-011, MK-3475), PD-L1 (MDX-1105 (BMS-936559), MPDL3280A, MSB0010718C), PD-L2 (rHIgM12B7), CTLA-4 (Ipilimumab (MDX-010), Tremelimumab (CP-675,206)), IDO, B7-H3 (MGA271), B7-H4, TIM3, LAG-3 (BMS-986016).

Human monoclonal antibodies to programmed death 1 (PD-1) and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

In some embodiments, the PDL1 inhibitor comprises an antibody that specifically binds PDL1, such as BMS-936559 (Bristol-Myers Squibb) or MPDL3280A (Roche). In some embodiments, the PD1 inhibitor comprises an antibody that specifically binds PD1, such as lambrolizumab (Merck), nivolumab (Bristol-Myers Squibb), or MEDI4736 (AstraZeneca). Human monoclonal antibodies to PD-1 and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

The disclosed compositions can be used in combination with other cancer immunotherapies. There are two distinct types of immunotherapy: passive immunotherapy uses components of the immune system to direct targeted cytotoxic activity against cancer cells, without necessarily initiating an immune response in the patient, while active immunotherapy actively triggers an endogenous immune response. Passive strategies include the use of the monoclonal antibodies (mAbs) produced by B cells in response to a specific antigen. The development of hybridoma technology in the 1970s and the identification of tumor-specific antigens permitted the pharmaceutical development of mAbs that could specifically target tumor cells for destruction by the immune system.

The compositions disclosed can be used therapeutically in combination with a pharmaceutically acceptable carrier. The carrier would naturally be selected to minimize any degradation of the active ingredient and to minimize any adverse side effects in the subject, as would be well known to one of skill in the art.

The herein disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vaginally, rectally, intranasally, topically or the like, including topical intranasal administration or administration by inhalant.

A number of embodiments of the invention have been described. Nevertheless, it will be understood that various modifications may be made without departing from the spirit and scope of the invention. Accordingly, other embodiments are within the scope of the following claims.

EXAMPLES

Example 1: STK11 Loss of Function is Associated with Immune Suppression Potentially Driven by Non-Canonical Polyamine Metabolism Methods
Acquisition of Publicly Available Genomic and Proteomic Datasets The TOGA LuAD dataset was downloaded from the Xena browser for gene expression (RNAseq), protein expression (RPPA), and somatic mutation. MLOS (GSE72094) has been previously described (Schabath M B, et al. Oncogene. 2016 35(24):3209-16; Chen Z, et al. J Clin Invest. 2016 126(6):2267-79; Chen L, et al. Oncotarget. 2016 7(50): 82254-65; Chen L, et al. J Thorac Oncol. 2016 11(16):838-49; Fan C, et al. Br J Cancer. 2015 113(12):1735-43; Cao C, et al. J Natl Cancer Inst. 2015; 107(1):358; Kutmon M, et al. PLoS Comput Biol. 2015 11(2):e1004085; Pluskal T, et al. BMC Bioinformatics. 2010 11:395).

Statistical Analysis

Statistical analysis was performed using the Scipy python package and the function scipy.stats.ttest_ind for p-value between gene arrays. Bonferroni correction was used by multiplying the p-value by the number of genes in the study. Pearson correlation was calculated through the scipy.stats.pearsonr function.

Public Gene-Set Enrichment Software

Two publically available methods of gene-set enrichment were used in this study. Genemania available as a web-based software was used on overlaps between TOGA and MLOS by t-test for both the 29 and 137 length gene-sets. Similarly, Broad Institute's Hallmark gene-sets were used with a FDR cutoff of 0.05.

Pathway Schematics

Pathways were generated using the PathVisio software.

K-Means Clustering Gene-Set Enrichment

This method of gene-set enrichment is performed on two-predefined populations of samples (STK11 mutant and wildtype). A database of gene-sets is clustered into (k=2) populations using K-means clustering through the Biopython library and the Bio.Cluster.kcluster function. The average method was used and Euclidean distance with 100 permutations. Upon clustering into two populations by each gene-set, a Fisher Exact test is used to statistically calculate how well the gene-set was able to cluster the patients into the predefined subsets. The scipy.stats.fisher_exact function was used for the statistical test.

Generation of Signature Scores

Principal component analysis was run through the Biopython library using the Bio.Cluster pca function. The data matrix was refined to the genes of interest prior to calculating component scores of each gene. The principal component was chosen which explained the largest variance between STK11 mutant and wildtype patients (PC1). Component scores were averaged between TCGA and MLOS and used for calculating a gene expression signature in each dataset.

Signature scores were generated by first calculating the number of standard deviations from the mean (z-score) for each gene for each patient. The averaged principal component loading coefficients were averaged between both TCGA and MLOS for each gene and were multiplied by the z-score. This cumulative score was then divided by the number of genes in the signature to get an average score per gene.

Immunohistochemistry and Scoring

Slides were stained using a Leica Bond RX automated system (Leica Biosytems, Buffalo Grove, IL) per the manufacturer's protocol with proprietary reagents. Briefly, slides were deparaffinized on the automated system with Dewax Solution (Leica). Heat induced antigen retrieval was performed using Epitope Retrieval Solution 2. The rabbit primary antibody that reacts to CD117 (#117R-14, Cell Marque, Rocklin, CA) was used at a 1:100 concentration in Dako diluent (Carpenteria, CA) and incubated for 25 min. The Leica Bond Polymer Refine Detection System was used. Post primary was incubated for 8 min. Polymer was used for 8 min. Slides were then counterstained with Hematoxylin. Slides were dehydrated and cover slipped per normal laboratory protocol.

Scoring of tissue microarray (TMA) slides was accomplished by using Leica Biosystems Aperio eSlide Manager online software. Each core of the TMA was segmented and used to calculate percentage of positive pixels for the respective stain, as previously described (Chen L, et al. J Thorac Oncol. 2016 11(16):838-49).

Western Blotting and Antibodies

Antibodies were diluted to working concentrations in PBST with 5% milk. The ODC1 antibody (ab193338), a mouse monoclonal antibody from Abcam, was used at a dilution of 1:400. The STK11 (LKB1) antibody, a rabbit monoclonal antibody from Cell Signaling (27D10) #305, was used at a dilution of 1:1,000. The β-actin antibody (SAB1305567), from Sigma-Aldrich, was used at a dilution of 1:20,000. The Li-COR Odyssey Fc was used to determine protein detection. Blots were developed for 10 minutes using the chemiluminescent channel.

Metabolomics Analysis by LC-MS

Frozen lung tumor samples (~10 mg) were homogenized in 40 mM ammonium formate using 1.0 mm zirconia beads in a BeadBeater (Biospec Products, Bartlesville, Okla.). Insoluble material was pelleted and the protein concentration of the supernatant was used for quality control and normalization. Stable isotope-labeled standards (SIS) including 1 mg/mL of D3-cysteine, 13C-alanine, 13C-methionine, 13C-arginine, D3-serine, D3-S-(5'-adenosyl)-L-methionine (SAM) and 1 μg/mL of 13C4-putrescine, 13C5-ornithine, D8-spermidine, and D8-spermine (Cambridge Isotope Labs, Tewksbury, MA) were added to each homogenate followed by 800 μL of acetonitrile:methanol:acetone (8:1:1) to precipitate proteins. The supernatant containing metabolites was lyophilized, re-suspended in 50 μL water and analyzed with LC-MS (Vanquish UHPLC and Q Exactive HF mass spectrometer, Thermo, San Jose, CA). For targeted quantification of metabolites in the polyamine pathway, peak areas were determined using Xcalibur QuanBrowser (v. 3.0.63) and amounts (in ng/mg total protein or mg tumor wet weight) were calculated using the peak area ratio of each molecule to its respective SIS. For untargeted analysis, LC-MS data files were converted to mzml files and analyzed using MZmine 2.25.

Data processing steps for the other detected metabolites (not involved in the polyamine pathway and without matched stable isotope-labeled standards) consisted of several steps: mass detection, chromatogram building, smoothing, chromatogram deconvolution, grouping of isotopic peaks, peak alignment with m/z tolerance of 5 ppm and retention time tolerance of 0.25 min, gap filling to fill in missing peaks, duplicate peak removal, and peak filtering (retention time range 0.45-17.0 min, peak duration range 0.06-2.00 min).

Gene Set Enrichment Analysis

Figures 1B, 1C:
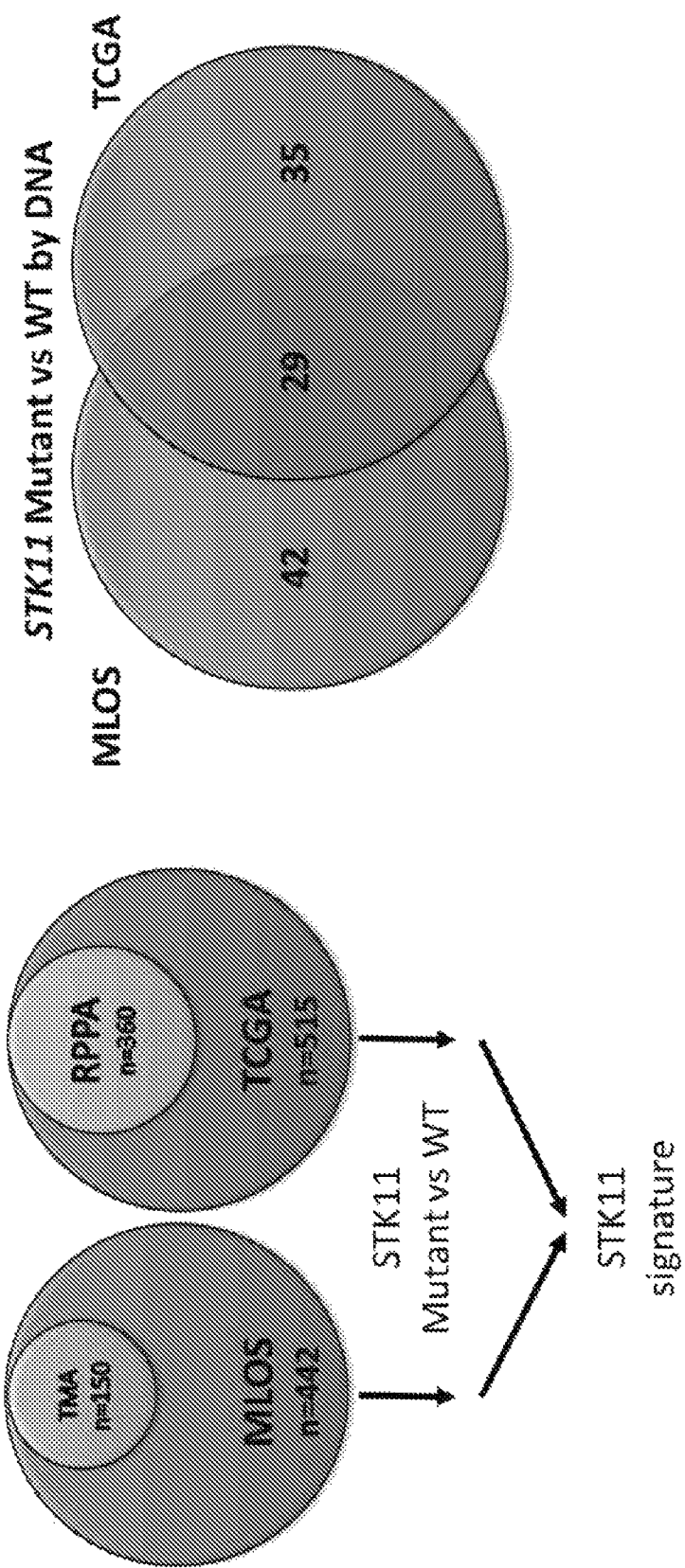
Figure 1D:
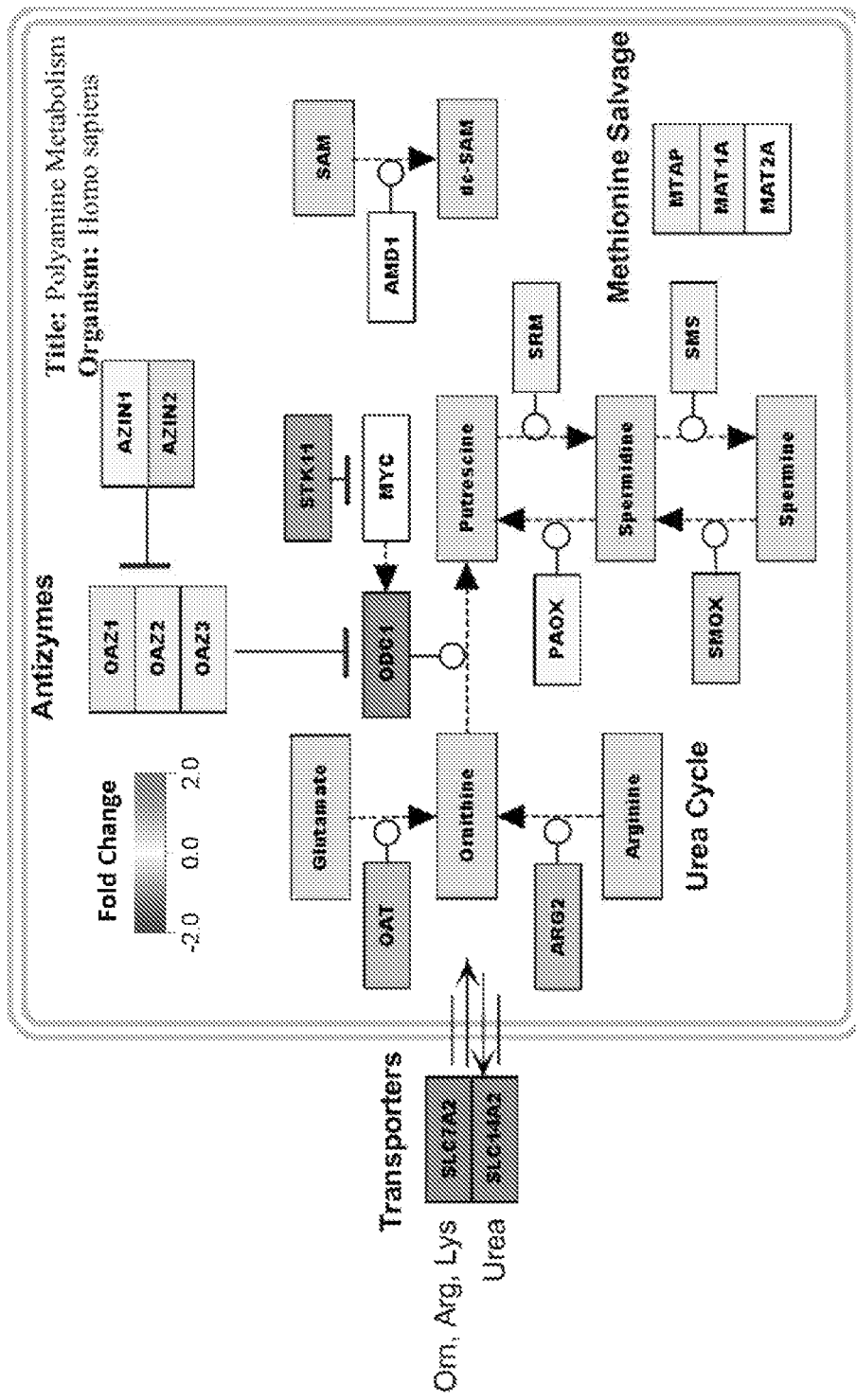

Utilizing MSigDB's Hallmarks genesets and looking for enrichment in the list of 29 genes revealed that only Hypoxia showed statistical significance (FDR=1.23e-2) with INHA, IRS2, and PPARGC1A overlapping between genesets (FIG. 1D bottom). However, when using Genemania nitrogen metabolism is revealed as significantly altered by means of these 3 pathways: alpha-amino acid metabolic process (FDR=3.63e-5), cellular amino acid catabolic process (FDR=6.06e-4), and transaminase activity (FDR=1.51e-2). This enrichment algorithm supports the observation that gene expression changes related to STK11 mutation upregulate amino acid catabolism, resulting in the accumulation of the toxic metabolite ammonia (FIG. 1D top).

Results

Gene Expression Patterns of STK11 Mutants by DNA-Sequencing

According to TCGA's pan-cancer study, DNA mutations of STK11 are most commonly found in large cell neuroendocrine lung tumors at a rate of 33% followed by LUADs at 18% (FIG. 1A). Gene expression-based classifiers have been reported that can distinguish STK11 mutated tumors from those with wildtype STK11 (Schabath M B, et al. Oncogene 2016 35(24):3209-16; Cao C, et al. J Natl Cancer Inst. 2015 107(1):358; Chen L, et al. J Thorac Oncol 2016 11(6):838-49; Kaufman J M, et al. Cancer Res 2017 77(1):153-63). In the present work, this gene expression analysis is extended to in vivo data. The first goal was to characterize similarities between RNA expression changes in two well annotated LUAD datasets: TCGA (N=515) and Moffitt's MLOS (N=442) (FIG. 1B). Each of these datasets contains both DNA sequencing and RNA expression data on the majority of patients. The initial test involved determining which patients had a sequenced STK11 mutation in each dataset and comparing them to their (wildtype) un-mutated counterpart. TCGA contained 76 mutant patients by DNA-sequencing and 409 confirmed wildtype patients while MLOS contained 68 and 374 respectively (Table 1). In each study only the genes changing by at least +/−1.5 Fold and with a Bonferroni corrected p-value of <1e-10 by student's t-test was further considered. TCGA had 64 genes that surpassed these criteria and MLOS contained 74 genes. Taken together, 29 genes overlapped and were used for gene set enrichment (FIG. 1C and Table 2). Upon closer examination, 5 STK11 mutant patients' tumors show a significant up-regulation of several solute transporters (SLC7A2, SLC14A2, and SLC16A4) (Table 2). SLC7A2 is known to be responsible for the membrane transport of cationic amino acids arginine, lysine, and ornithine. SLC14A2 is surprisingly responsible for the transport of urea and is the end result of nitrogen detoxification. SLC16A14 (MCT14) is part of the monocarboxylate transporter family and has been shown to be highly abundant in both the kidney and central nervous system. This family of transporters is known for their transfer of carboxylic acids. In addition to these family of transporters there was also a consistent upregulation of CPS1 (Carbamoyl-phosphate synthase 1), which has previous been associated with pathway disruption of STK11 (Celiktas M, et al. J Natl Cancer Inst 2017 109(3):1-9; Kim J, et al. Nature 2017 546(7656):168-72), and ODC1 (ornithine decarboxylase), which has not been previously associated with STK11. Taken together, these genes cooperate in the regulation of the urea cycle, with CPS1 being responsible for the initial incorporation and removal of both ammonia and bicarbonate and ODC1 catalyzing the rate limiting step of polyamine biosynthesis from ornithine, another urea cycle intermediate. Genes regulating transport suggest that these cells are increasing their flux of the transport of ornithine, arginine, and urea which further point to the enrichment of this liver-associated biological pathway. Using the 29 genes in gene set enrichment analyses support the conclusion that the polyamine pathway, highlighted in FIG. 1D, is dramatically altered in STK11 mutant tumors.

TABLE 1

STK11 mutant statistics and signature prediction

| | WT Sig (N, (%)) | Mutant Sig (N, (%)) | Total (N, (%)) |
|---|---|---|---|
| MLOS | | | |
| WT DNA | 297 (67.2) | 77 (17.4) | 374 (84.6) |
| Mutant DNA | 0 (0) | 68 (15.4) | 68 (15.4) |
| Total | 297 (67.2) | 145 (32.8) | 442 (100) |
| TCGA | | | |
| WT DNA | 314 (61.0) | 95 (18.4) | 409 (79.4) |
| Mutant DNA | 4 (0.80) | 72 (14.0) | 76 (14.8) |
| Unknown | 19 (3.7) | 11 (2.1) | 30 (5.8) |
| Total | 337 (65.5) | 178 (34.5) | 515 (100) |

TABLE 2

STK11 DNA mutation related gene expression changes

| Gene | MLOS BF p-value | MLOS FC | MLOS Rank | TCGA BF p-value | TCGA FC | TCGA Rank | Average Rank | Average FC |
|---|---|---|---|---|---|---|---|---|
| LINC00473 | 3.3E−32 | 6.70 | 1 | 1.56E−29 | 26.96 | 1 | 1.0 | 16.83 |
| SLC16A14 | 1.19E−31 | 6.06 | 2 | 7.95E−24 | 6.07 | 3 | 2.5 | 6.06 |
| PDE4D | 4.63E−20 | 2.73 | 6 | 2.8E−26 | 3.74 | 2 | 4.0 | 3.23 |
| ODC1 | 1.42E−25 | 2.62 | 3 | 1.49E−20 | 3.59 | 7 | 5.0 | 3.10 |
| INHA | 1.91E−19 | 4.34 | 7 | 6.59E−23 | 14.46 | 4 | 5.5 | 9.40 |
| SLC7A2 | 1.27E−22 | 4.50 | 4 | 1.92E−20 | 7.01 | 8 | 6.0 | 5.75 |
| CPS1 | 7.06E−19 | 4.88 | 9 | 5.68E−21 | 28.80 | 6 | 7.5 | 16.84 |
| SLC14A2 | 1.85E−22 | 4.34 | 5 | 3.52E−19 | 12.72 | 10 | 7.5 | 8.53 |
| DUSP4 | 4.21E−18 | 2.94 | 10 | 3.71E−18 | 4.10 | 11 | 10.5 | 3.52 |
| IRS2 | 5.08E−16 | 2.02 | 16 | 7.69E−23 | 3.29 | 5 | 10.5 | 2.65 |
| FXYD4 | 1.3E−17 | 2.41 | 11 | 2.22E−16 | 7.86 | 15 | 13.0 | 5.13 |
| GLTPD2 | 2.18E−15 | 2.21 | 17 | 3.96E−18 | 7.10 | 12 | 14.5 | 4.65 |
| INSL4 | 3.22E−17 | 5.71 | 14 | 3.01E−14 | 9.25 | 18 | 16.0 | 7.48 |
| BAG1 | 4.11E−15 | 1.57 | 20 | 3.22E−17 | 1.89 | 13 | 16.5 | 1.73 |
| FGL1 | 2.82E−15 | 6.73 | 18 | 5.32E−15 | 17.50 | 16 | 17.0 | 12.11 |
| HAL | 6.91E−15 | 3.79 | 21 | 8.55E−17 | 6.72 | 14 | 17.5 | 5.26 |
| PPARGC1A | 1.86E−16 | 3.14 | 15 | 3.39E−14 | 5.17 | 20 | 17.5 | 4.16 |
| KSR1 | 1.98E−19 | 1.92 | 8 | 2.97E−11 | 2.12 | 29 | 18.5 | 2.02 |
| KCNU1 | 5.36E−11 | 2.09 | 29 | 2.44E−19 | 4.56 | 9 | 19.0 | 3.32 |
| GALNTL6 | 1.85E−17 | 4.49 | 12 | 1.21E−11 | 3.36 | 28 | 20.0 | 3.93 |
| EYS | 2.01E−17 | 2.19 | 13 | 7.95E−12 | 3.00 | 27 | 20.0 | 2.60 |
| CALCA | 3.44E−15 | 7.31 | 19 | 7.95E−13 | 20.24 | 24 | 21.5 | 13.77 |
| TACC2 | 2.25E−13 | 2.18 | 24 | 3.18E−14 | 2.56 | 19 | 21.5 | 2.37 |
| ADSSL1 | 2.65E−11 | 2.06 | 28 | 1.96E−14 | 2.68 | 17 | 22.5 | 2.37 |
| FURIN | 4.85E−14 | 1.65 | 22 | 3.08E−13 | 2.33 | 23 | 22.5 | 1.99 |
| AIM1 | 1.21E−13 | −2.08 | 23 | 2.5E−13 | −2.54 | 22 | 22.5 | −2.31 |
| BMP6 | 5.95E−13 | 2.70 | 25 | 1.97E−13 | 3.82 | 21 | 23.0 | 3.26 |
| PDE3A | 2.26E−11 | 2.47 | 27 | 8.53E−13 | 3.92 | 25 | 26.0 | 3.20 |
| VPS37A | 1.2E−12 | 1.91 | 26 | 3.65E−12 | 1.61 | 26 | 26.0 | 1.76 |

Expansion and Classification of Patients with STK11 Loss

Figure 2A:
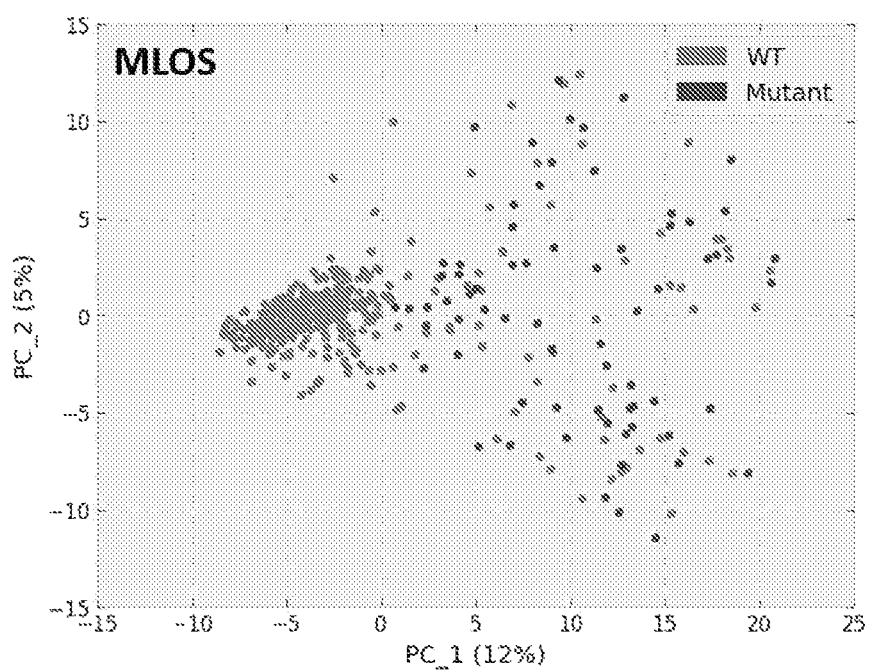
Figure 2B:
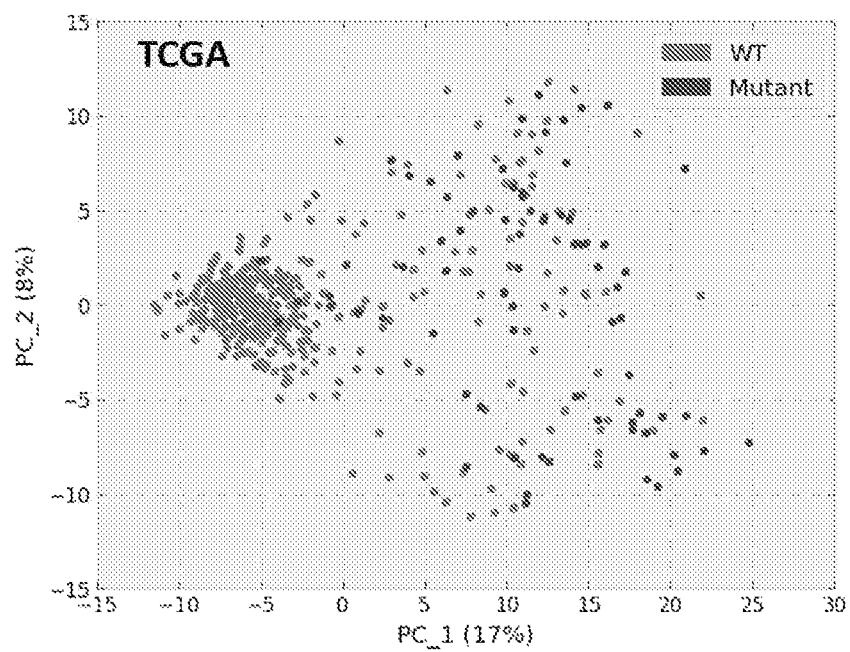
Figure 2C:
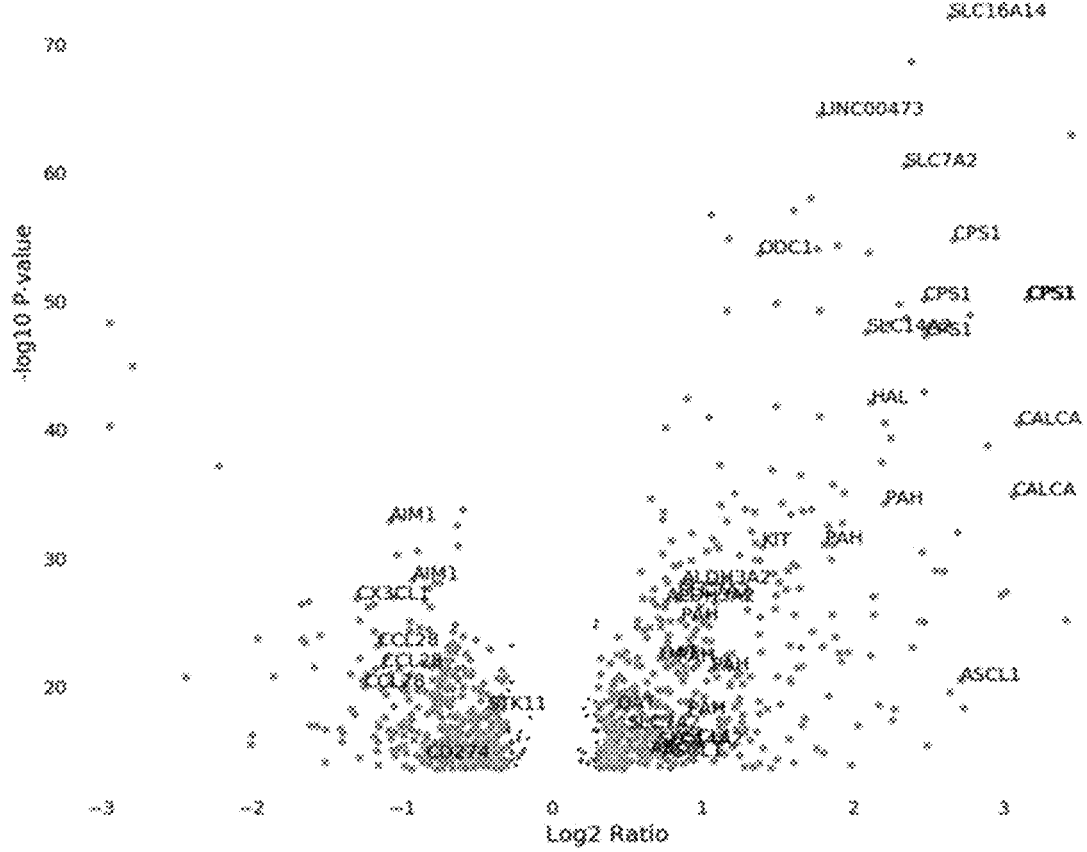
Figure 2D:
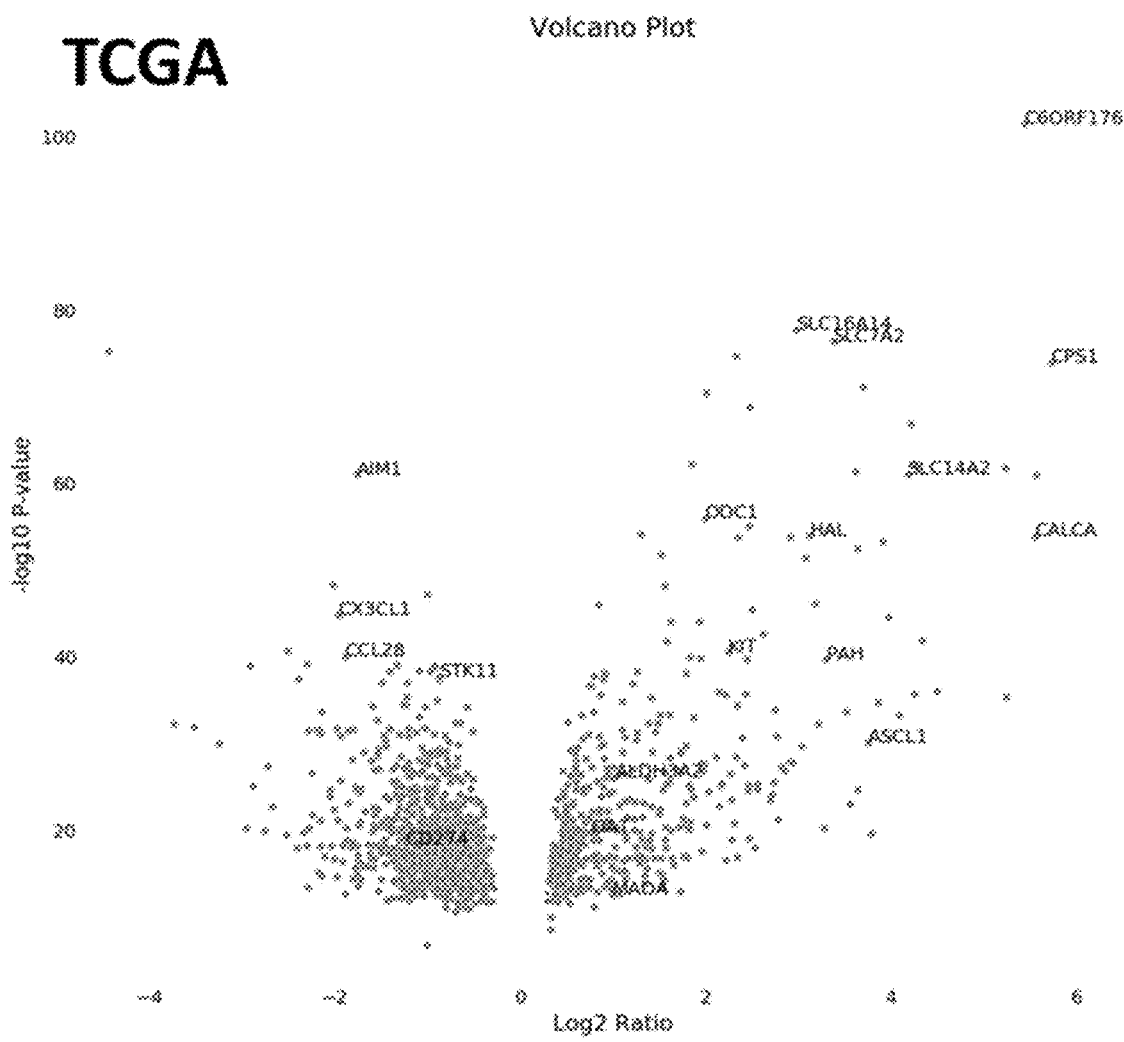
Figure 2E:
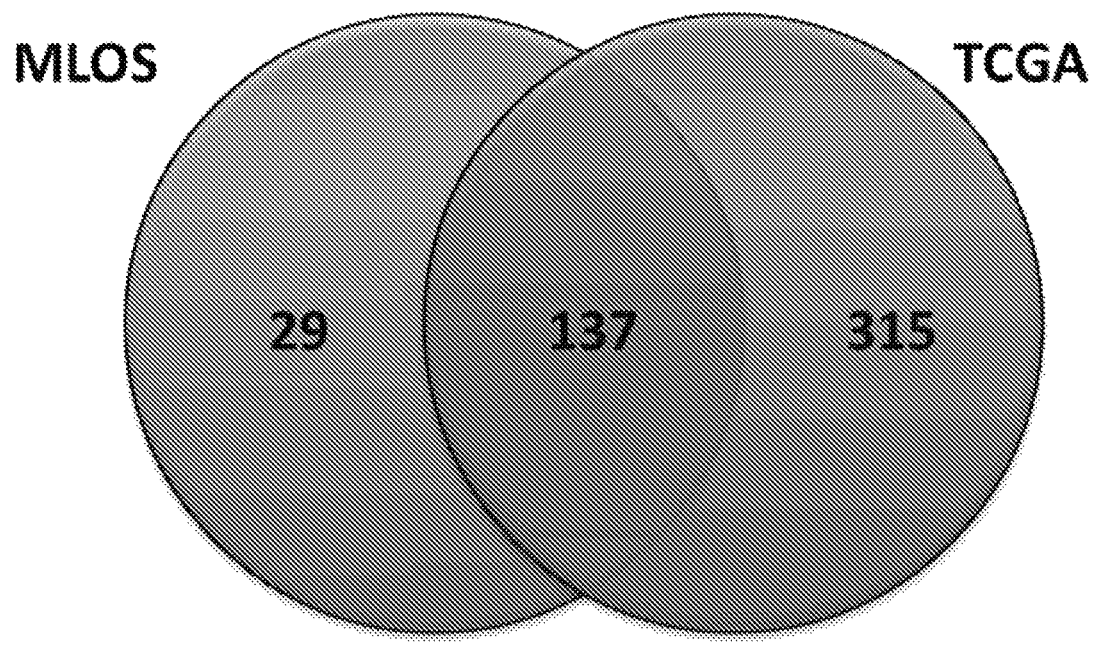

It was hypothesized that DNA sequencing would only reveal a portion of patients with the same phenotype of STK11 mediated pathway disruption with chromosomal loss of 19p13, methylation of the STK11 allele, or alterations in up or downstream pathways accounting for STK11 loss-of-function without mutation. When using the 29-gene signature as a classifier for STK11 status and utilizing principal component analysis (PCA) in LUAD patients in both TOGA and the MLOS it was discovered that nearly twice as many patients have gene expression patterns imitating mutations in STK11 based on the 1st principal component (PC1) (FIGS. 2A and B). Thus, a signature score was derived based on PC1 coefficients from TOGA and MLOS cohorts (Table 3) to reclassify patient STK11 loss with a signature score greater than 0 were classified as mutant and less than 0 were classified as wildtype. Upon reclassification of patients into either mutant-like or wildtype, these new cohorts were analyzed for gene expression changes (FIGS. 2C and D). The volcano plot of genes changing as a result of STK11 loss of function reveal far more upregulated genes than down-regulated ones. With many patient tumors harboring expression patterns imitating that of an STK11 mutation and representing false negatives for detection of an STK11 mutation that were classified into the initial wildtype cohort, the first analysis was statistically weakened. While many of the hallmarks of STK11 pathway disruption remained constant in this new analysis, many others now surpassed the threshold of statistical significance. By keeping the threshold of a fold change of +/−1.5 consistent, Bonferroni corrected p-value was increased to only include genes with a value of less than 1 e-15. Even with this increase in stringency there were statistically relevant changes in 451 genes in TOGA and 165 genes in the MLOS, with 137 genes overlapping between both of these datasets (FIG. 2E). All genes upon re-classification have much greater statistical significance and fold changes. It is worth noting that the long non-coding RNA annotated as both LINC00473 and C6ORF176 are consistently the best marker of STK11 loss of function in both studies (Chen Z, et al. J Clin Invest 2016 126(6):2267-79).

TABLE 3

STK11 signature gene PCA coefficients

| Gene | TCGA PC1 | MLOS PC1 | Average PC1 |
| --- | --- | --- | --- |
| CPS1 | 0.3739 | 0.2756 | 0.3248 |
| CALCA | 0.3737 | 0.2567 | 0.3152 |
| FGL1 | 0.3470 | 0.2375 | 0.2922 |
| LINC00473 | 0.3284 | 0.2099 | 0.2692 |
| INSL4 | 0.2224 | 0.1950 | 0.2087 |
| INHA | 0.2620 | 0.1553 | 0.2087 |
| SLC14A2 | 0.2500 | 0.1491 | 0.1995 |
| SLC7A2 | 0.2101 | 0.1646 | 0.1874 |
| SLC16A14 | 0.1811 | 0.1798 | 0.1804 |
| HAL | 0.1917 | 0.1554 | 0.1736 |
| PPARGC1A | 0.1820 | 0.1337 | 0.1579 |
| DUSP4 | 0.1519 | 0.1396 | 0.1457 |
| FXYD4 | 0.2094 | 0.0820 | 0.1457 |
| BMP6 | 0.1579 | 0.1235 | 0.1407 |
| GLTPD2 | 0.1768 | 0.0789 | 0.1279 |
| GALNTL6 | 0.1103 | 0.1416 | 0.1259 |
| KCNU1 | 0.1529 | 0.0829 | 0.1179 |
| PDE3A | 0.1303 | 0.1033 | 0.1168 |
| PDE4D | 0.1169 | 0.1016 | 0.1092 |
| ODC1 | 0.1222 | 0.0959 | 0.1090 |
| IRS2 | 0.1113 | 0.0759 | 0.0936 |
| EYS | 0.1092 | 0.0681 | 0.0886 |
| TACC2 | 0.0889 | 0.0770 | 0.0829 |
| FURIN | 0.0940 | 0.0564 | 0.0752 |
| ADSSL1 | 0.0743 | 0.0759 | 0.0751 |
| KSR1 | 0.0771 | 0.0697 | 0.0734 |
| VPS37A | 0.0519 | 0.0706 | 0.0612 |
| BAG1 | 0.0488 | 0.0431 | 0.0459 |
| AIM1 | −0.1045 | −0.0760 | −0.0902 |

Figure 2G:
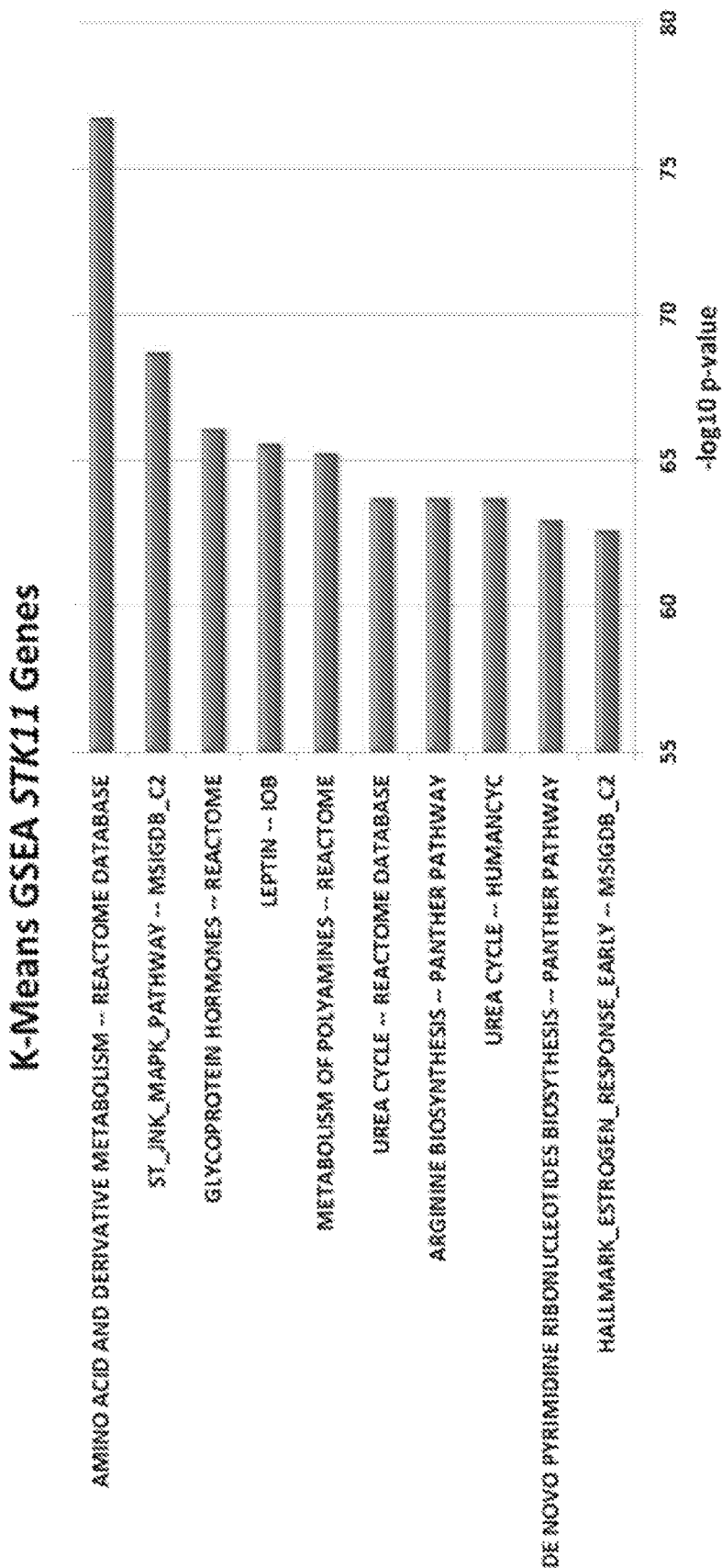

Predicted STK11 Loss is Associated with Changes in Nitrogen Metabolism and the Immune Microenvironment Following expansion of the STK11 pathway disruption signature, GSEA was re-run on the 137 genes. This time, MSigDB's Hallmarks revealed enrichment in Inflammatory Response (FDR=8.77e-13), Interferon Gamma Response (FDR=8.77e-13), as well as Interferon Alpha Response (FDR=1.58e-8). This result is interesting because it supports the observation that disruption of the STK11 signaling pathway with respect to our signature involves an alteration of the inflammatory and immune response of the tumor microenvironment (FIG. 2F). These changes in the immune landscape may be influenced by metabolic alterations in the microenvironment resultant of an altered stress response. Genemania's enrichment was in support of this altered immune reactivity with the top biological processes being response to virus (FDR=1.1e-14) and response to type I interferon (FDR=9.17e-14). Using K-means enrichment algorithm described in Materials and Methods, it was discovered that gene sets pertaining to amino acid metabolism, polyamine metabolism, and the urea cycle were most significantly useful in distinguishing predicted STK11 mutant from wildtype tumors (FIG. 2G). Altogether, these data suggest that upregulation of amino acid catabolism, nitrogen processing through the urea cycle, and polyamine metabolism could be influencing the immune silent microenvironment seen in patients with STK11 mediated pathway disruption.

Figure 2H:
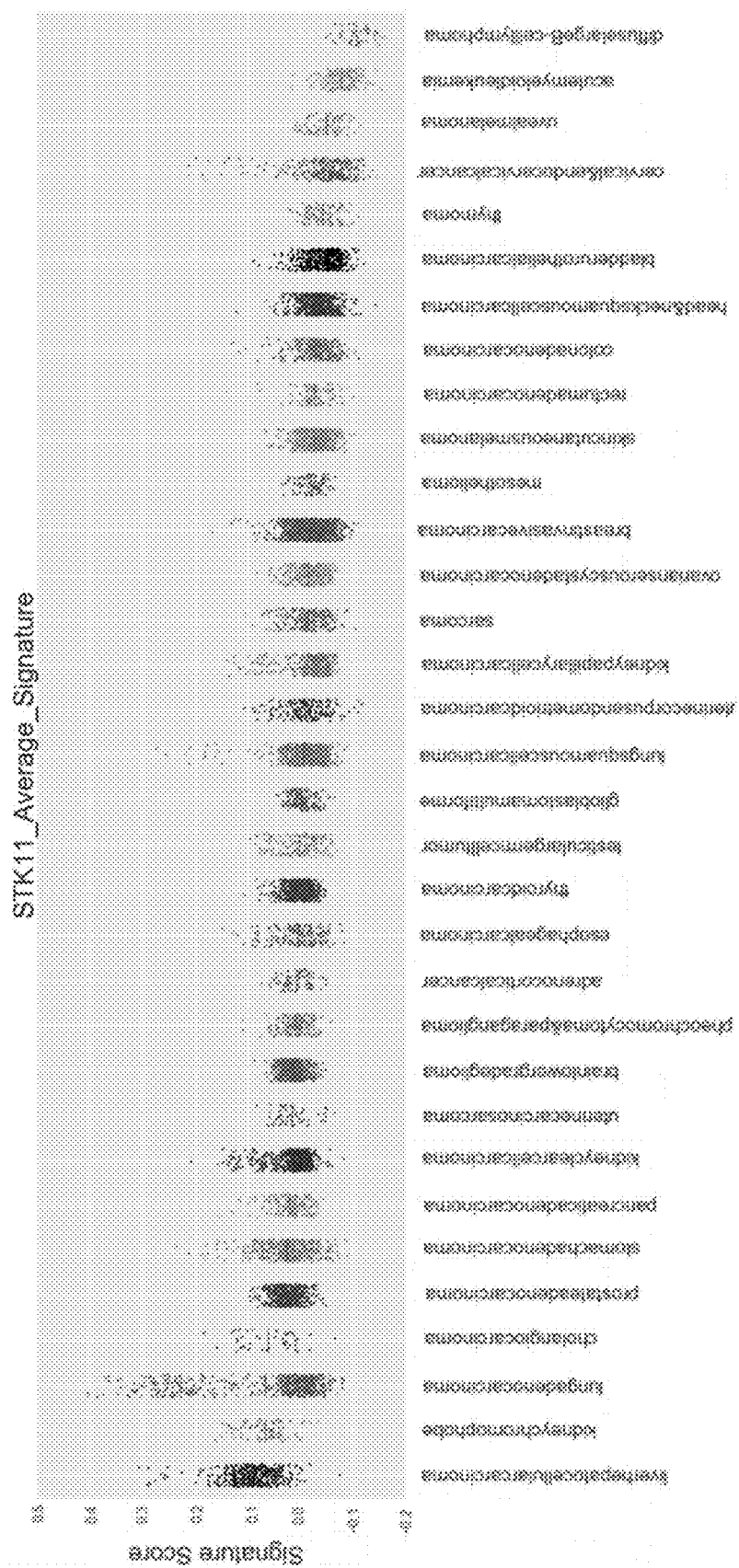

Additionally, it was thought it would be interesting to take the STK11 signature and apply it to each cancer type in TCGA's pan-cancer study. Patients with a high relative STK11 pathway disruption score exist in lung adenocarcinoma as shown, but also in cervical cancer, kidney papillary and clear cell carcinoma, breast cancer, lung squamous cell carcinoma, stomach adenocarcinoma, and liver hepatocellular carcinoma. Liver has the highest overall signature for STK11 loss than any other cancer by a good margin (FIG. 2H). The liver is a uniquely capable of responding uniquely in times of energy deprivation and utilizing amino acids and fats for energy (Rui L. Compr Physiol 2014 4(1):177-97). It is also the main site of the urea cycle, responsible for processing most of the body's excess nitrogen and excreting it in the form of urea. This observation fits the hallmark of STK11 loss very well and helps support this novel role of amino acid degradation.

ODC1 Elevation is Specific to Patient Tumors with STK11 Loss

Figures 3A, 3B:
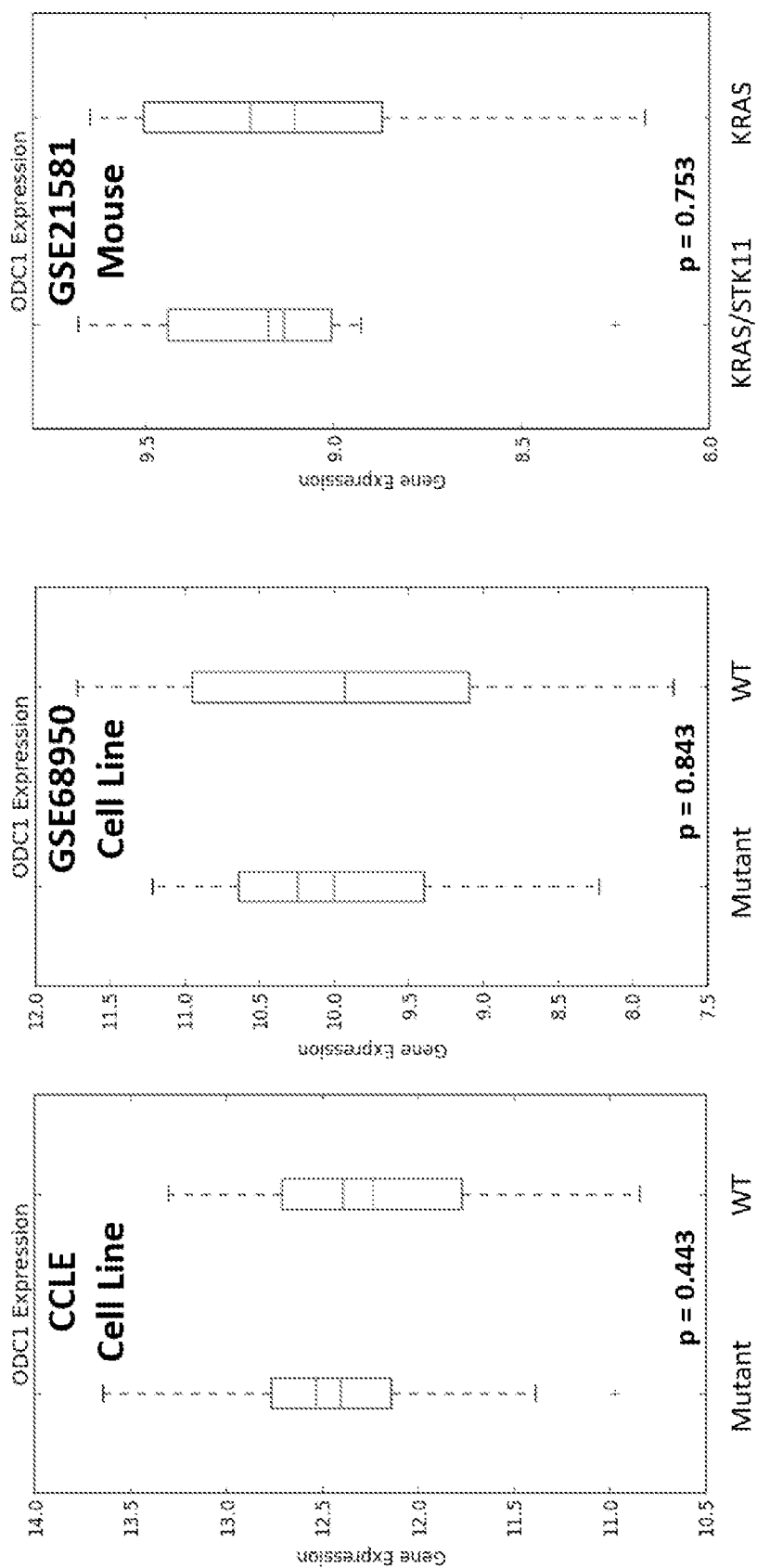
FIGS. 3A to 3E shows ODC1 elevation is specific to patient tumors.
Figures 3C, 3D:
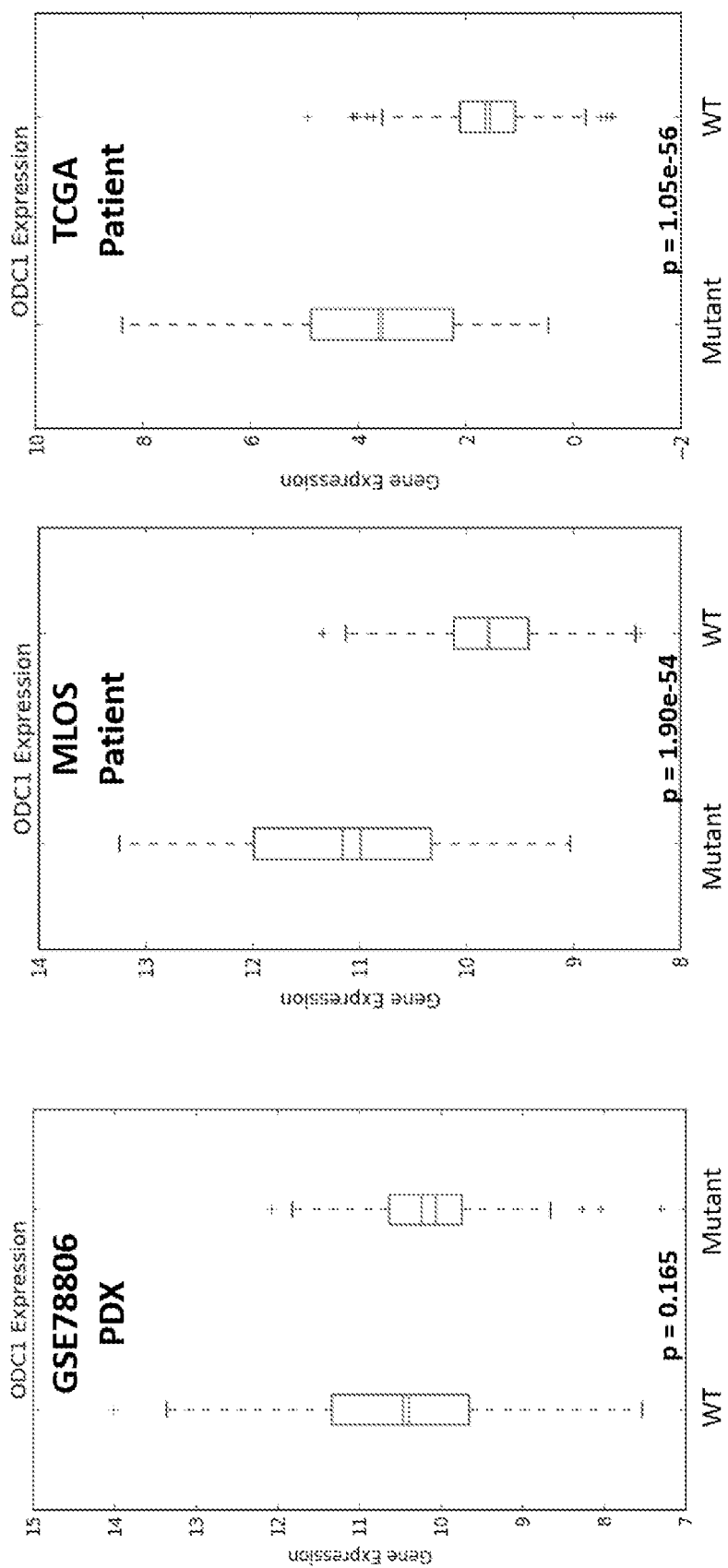

The next goal was to determine whether elevation of ODC1 could be studied outside the context of patient tumors with predicted STK11 loss. The patient tumor derived STK11 signature was applied to the following datasets: cell line datasets (GSE36133 and GSE68950) (FIG. 3A), patient derived lung xenografts (PDX) (GSE78806) (FIG. 3C), and patient datasets (MLOS and TOGA) (FIG. 3D). Additionally, the expression of ODC1 was characterized in Cre mouse studies of primary tumors between KRAS and KRAS/STK11 mice (FIG. 3B). Similar to the patient datasets, samples with a signature score higher than 0 were considered mutant-like and less than 0 wildtype. Cell line datasets (p=0.443 and 0.843), mouse models (p=0.753), and PDX models (p=0.165) of STK11 loss showed no significant change in ODC1 expression despite ODC1 being a significant driver of the STK11 signature.

Patients with STK11 Loss have Elevated Levels of ODC1 Protein

Figure 3E:
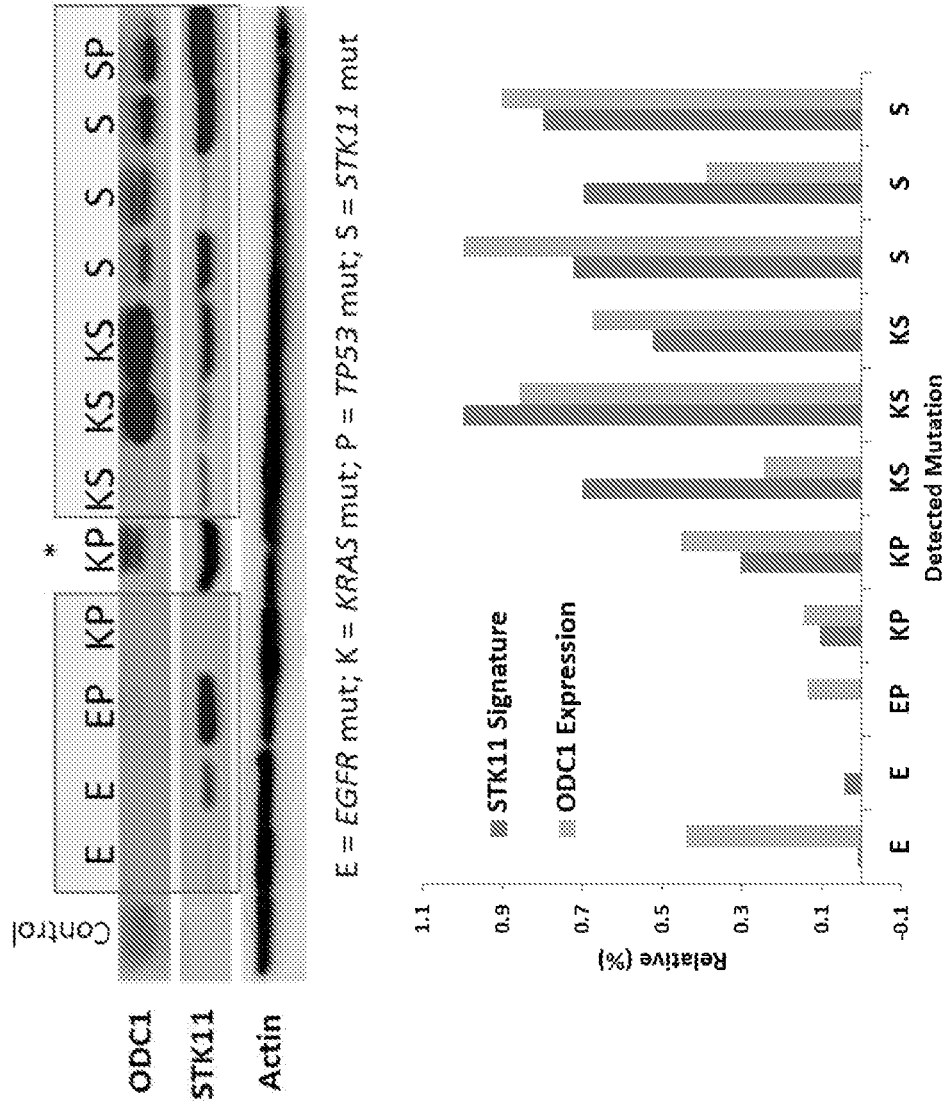

ODC1 is significantly elevated in patients with predicted STK11 loss of function (MLOS p=1.9e-54 and TOGA p=1.05e-56) (FIG. 3D). In order to validate whether or not tumors with STK11 mutations have a detectably higher level of ODC1 activity than WT tumors, a western blot was run on protein extracts from a dozen patient tumors from the MLOS cohort. This western blot was done on patients with detectable DNA level STK11 mutations and validates that there is a strong association between the levels of mRNA and functional protein (FIG. 3E). Further, ODC1 gene expression and STK11 loss signature score was then compared in these patients. There is a clear correlative relationship between the STK11 loss signature, ODC1 protein, and ODC1 gene expression.

STK11 Loss is Associated with a Lack of Immune Infiltration

One interesting pattern observed in the subset of patients with STK11 pathway disruption is the inverse relationship with immune components and inflammation (Schabath M B, et al. Oncogene 2016 35(24):3209-16; Scheel A H, et al. Oncoimmunology 2016 5(5):e113137). It was suspected that the lack of immune response is supported by the lack of tumor PD-L1 expression because it suggests that the immune evasion is through a mechanism independent of PDL-L1 activity. Several key elements of the immune response are notably reduced in STK11 mutant patients such as co-stimulatory molecules CD40 and CD80, antigen presentation in the form of MHC class I and II, immunoinhibitory ligands PD-L1 (CD274), inflammasome complex formation through AIM1, and chemotactic recruitment of cytotoxic cells in the form of CX3CL1 (McComb J G, et al. Am J Pathol 2008 173(4):949-61; Zhang J, et al. Int J Clin Exp Med 2010 3(3):233-44; Greene J A, et al. PLoS One 2015 10(12):e0144133; Madrigal J L, et al. Neuropharmacology 2017 114:146-55).

Figure 4A:
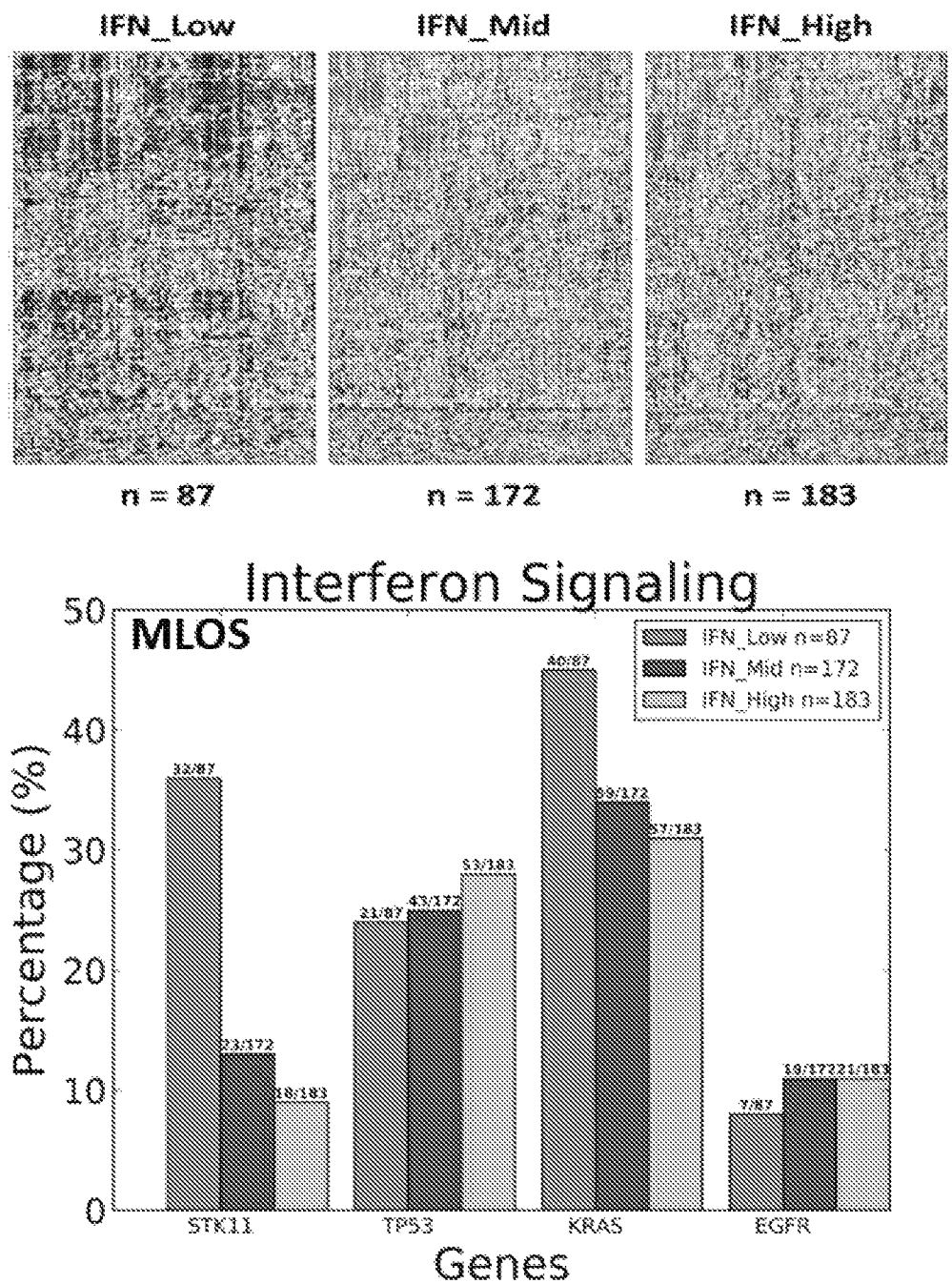
Figure 4B:
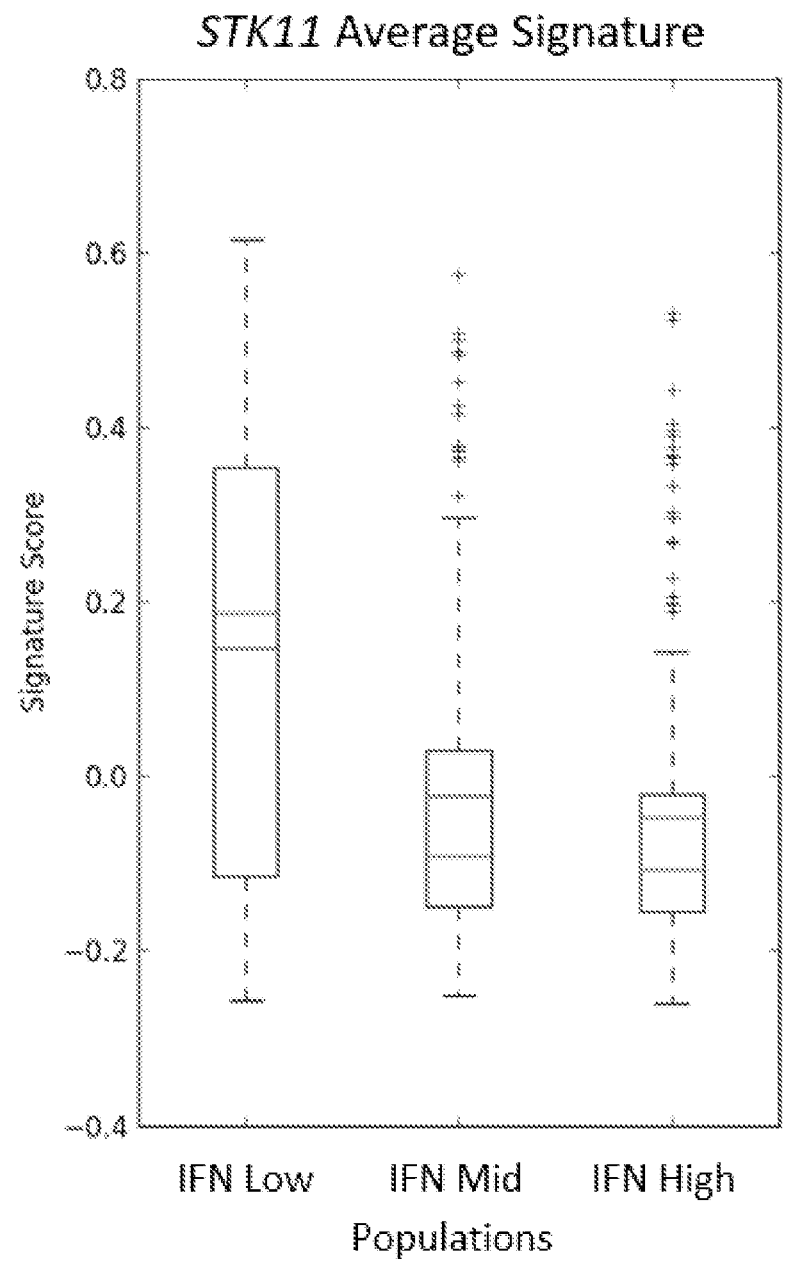
Figure 4C:
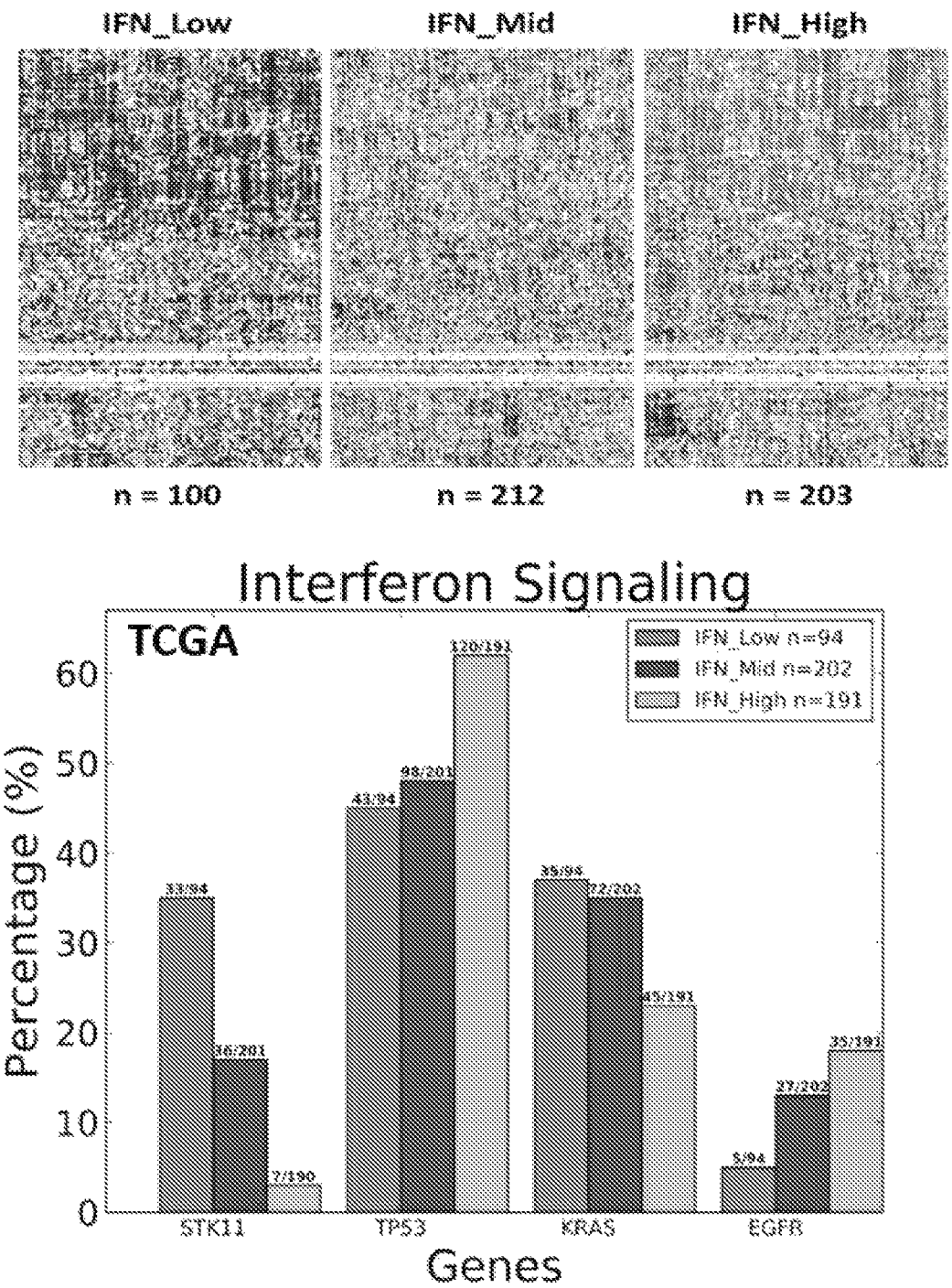
Figure 4D:
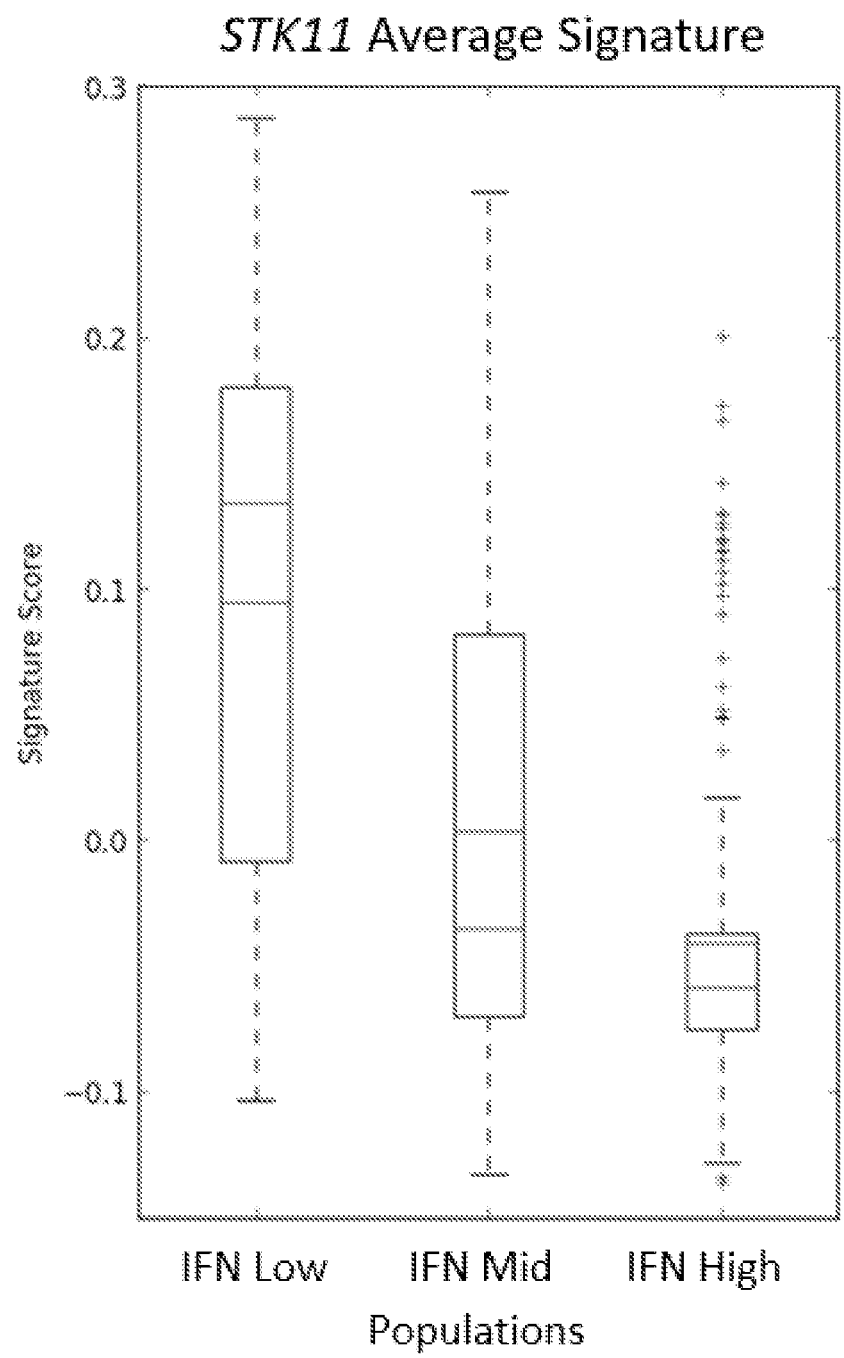
Figure 4E:
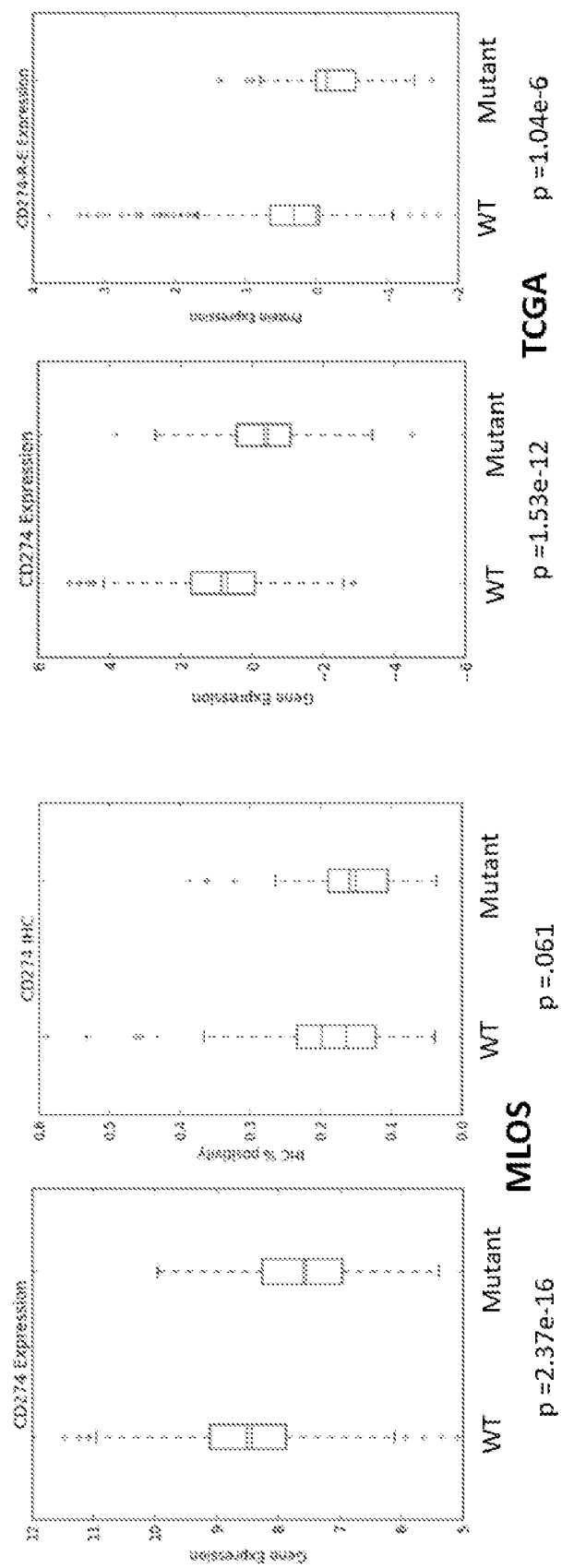

In order to further validate this observation in coordination with the gene set enrichment results PD-L1 abundance (CD274) was compared on both the mRNA and protein level between mutant and wildtype STK11 patients. Patients with an STK11 mutation have significantly lower amounts of PD-L1 mRNA ($p<1e-12$) and protein ($p=1.04e-6$) (FIG. 4E). This lack of PD-L1 expression may be due to the lack of T-cell infiltration and immune reactivity. In order to look more globally at the association between inflammation and STK11 status, lung adenocarcinoma patients were clustered by MsigDBs gene list for Interferon Signaling containing 159 gene symbols validated for this pathway. These data were used as a surrogate marker of immune activation in all LUAD patients. K-means clustering was used to separate both TOGA LUAD (n=515) and MLOS (n=442) into 3 distinct subpopulations (Interferon low, medium, and high) (FIGS. 4A and B). Both TOGA and MLOS clustered into similar distributions, with roughly 20% of samples falling into the Interferon Low subset (Table 4). Fisher's Exact test was used to analyze these populations for enrichments in DNA mutations (FIGS. 2B and 2D). In addition, the STK11 signature was applied to these clusters and there was a significant difference between Interferon low and high populations in both TOGA ($p=7.37e-33$) and MLOS ($p=4.06e-33$). STK11 is the leading mutation accounting for the changes in interferon signaling and is inversely related to Interferon levels between IFN_Low and IFN_High ($p=4.51E-12$) in TOGA and between IFN_Low and IFN_High ($p=4.29e-7$) in MLOS. It is interesting that mutations in EGFR and TP53 both trend in the direction opposite of STK11 mutations. This outcome is likely due to both of these mutations being mutually exclusive with STK11 suggesting preservation of the p16/TP53 signaling pathway in patients with STK11 loss as similar seen in large cell neuroendocrine tumors (Rekhtman N, et al. Clin Cancer Res 2016 22(14):3618-29). However, EGFR may be effecting interferon signaling through downstream kinase activity and TP53 is increasing neo-antigen levels and that both likely contribute to the increase in inflammatory signaling.

TABLE 4

Interferon gene-set K-means association with STK11 status

| | TCGA (N, (%)) | STK11 Mutation % | MLOS (N, (%)) | STK11 Mutation % |
|---|---|---|---|---|
| Low | 100 (19.42) | 35 | 87 (19.68) | 36 |
| Mid | 212 (41.17) | 17 | 172 (38.91) | 13 |
| High | 203 (39.42) | 3 | 183 (41.4) | 9 |

ODC1 and the Polyamine Pathway is Associated with Immune Suppression

Polyamines have been studied for decades and recent literature has shown the impact that polyamine inhibition can have on reversing tumor-associated immune suppression (Chamaillard L, et al. Br J Cancer 1997 76(3):365-70; Hayes C S, et al. Oncoimmunology 2014 3(1):e27360; Hayes C S, et al. Cancer Immunol Res 2014 2(3):274-85; Alexander E T, et al. Oncotarget 2017 8(48):84140-52). In order to determine if there was a relationship between ODC1 activity and the loss of PD-1 and PD-L1 observed in STK11 mutant patients the correlation between STK11 relevant genes and common immune markers was examined (FIGS. 4F and 4G). In order to answer this question in the appropriate context, only patients with predicted STK11 loss of function were used for the correlation, given that it has already shown that STK11 loss of function itself is associated with a lack of immune infiltration. By gene expression ODC1 has a strong inverse relationship to PD-1(PDCD1), CD8A, and PD-L1 (CD274) (FIGS. 4F and 4G). While correlation does not prove causation, this result is consistent with the relevance of ODC1 biology to the observed decrease in both cytotoxic T-cell markers and tumor intrinsic immune suppression in patients with loss of STK11.

Figure 5A:
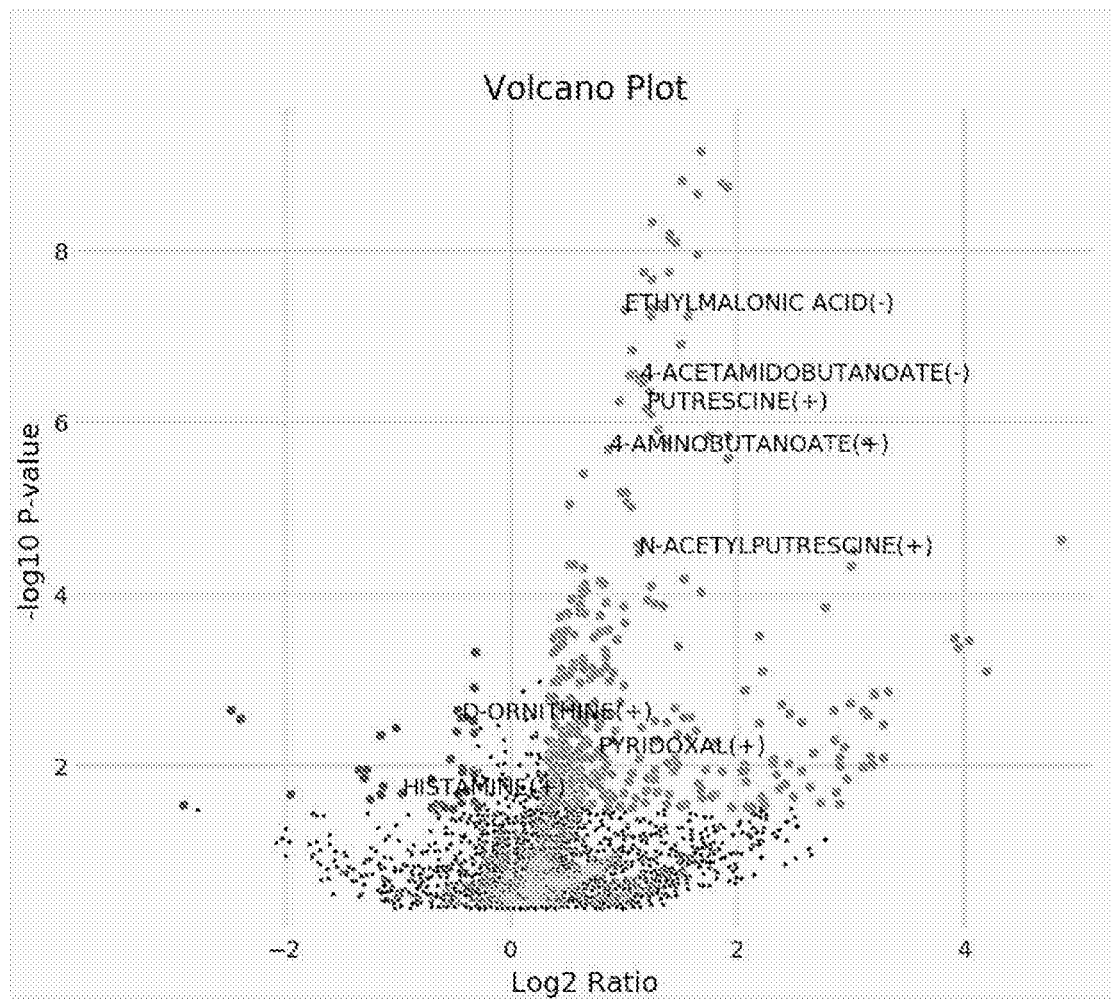
FIGS. 5A to 5D shows Putrescine and GABA elevated in patients with STK11 loss of function.
Figure 5C:
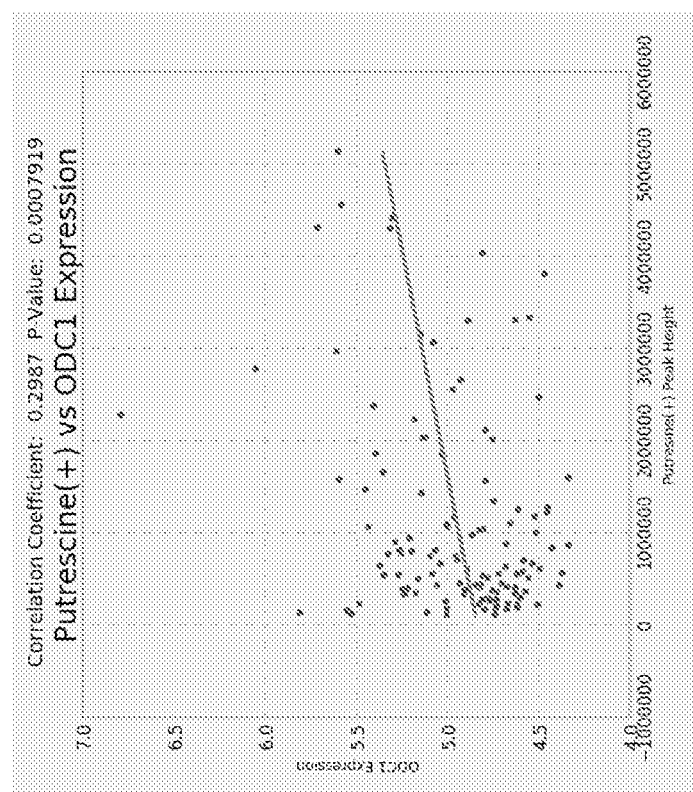
Figure 5B:
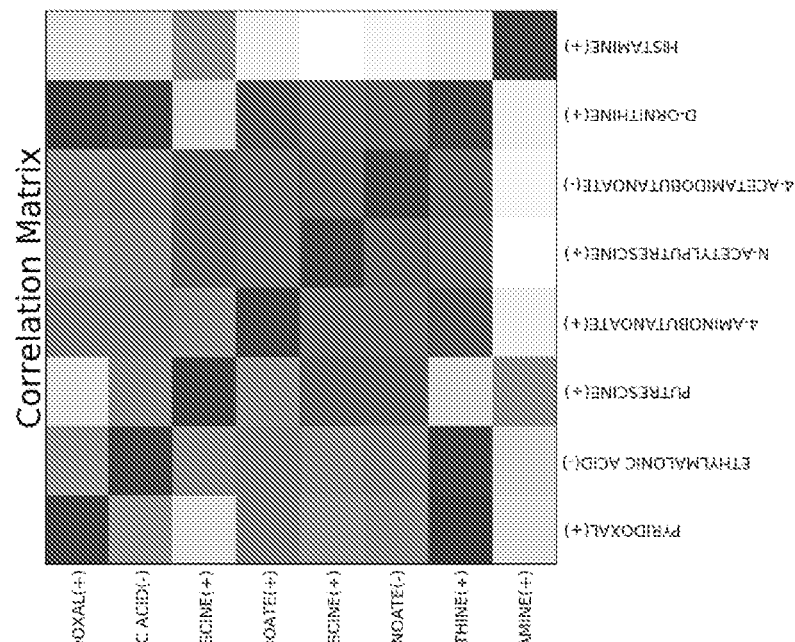

Increased Metabolite Production of Putrescine and GABA in Patients with STK11 Loss Following the discovery of both elevated ODC1 in patient tumors and its inverse relationship to inflammatory signaling, the next goal was to validate the hypothesis that this elevation was reshaping the microenvironment and could potentially explain changes in immune surveillance. In order to accomplish this, 126 patient samples of the TMA150 cohort were subjected to untargeted metabolite profiling using LC-MS and generated datasets containing over 6,200 features. Of these features, approximately 250 were identified by comparison to a library of metabolite standards. Using the STK11 signature in MLOS, differential features and metabolites were looked for as a result of predicted STK11 loss of function. In support of the hypothesis, putrescine was one of the most significantly elevated metabolites supporting increased ODC1 activity (FIG. 5A). Surprisingly, rather than the canonical downstream polyamines spermidine and spermine being elevated, there was an increase in 4-aminobutanoate, also known as gamma-aminobutyric acid (GABA) which had the strongest correlation to putrescine in our study (FIG. 5B). Additionally the acetylated counterparts of both putrescine and GABA were almost equally enriched (Table 5). The relationship of ODC1 to Putrescine was also examined, and there was a significant positive correlation ($r=0.30$, $p=0.0008$) (FIG. 5C).

TABLE 5

Metabolites elevated in predicted STK11 mutants

| Study Symbol | P-Value | Fold Change |
|---|---|---|
| ETHYLMALONIC ACID(−) | 4.87E−08 | 2.01 |
| 4-ACETAMIDOBUTANOATE(−) | 3.13E−07 | 2.18 |
| 4-ACETAMIDOBUTANOATE(+) | 5.65E−07 | 1.93 |
| PUTRESCINE(+) | 6.90E−07 | 2.28 |
| 4-AMINOBUTANOATE(+) | 2.11E−06 | 1.81 |
| N-ACETYLPUTRESCINE(+) | 3.33E−05 | 2.18 |

Figure 5D:
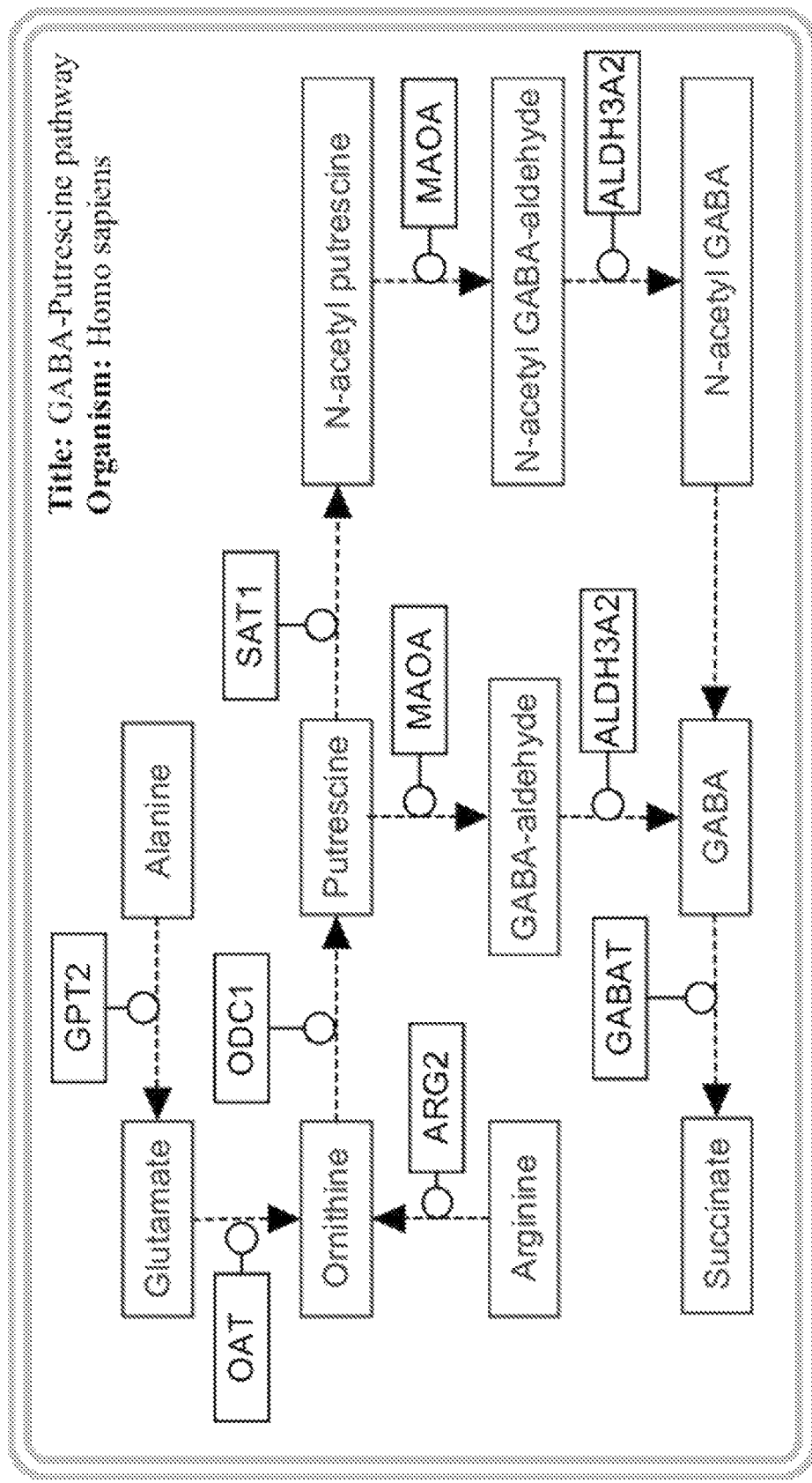
Figure 6:
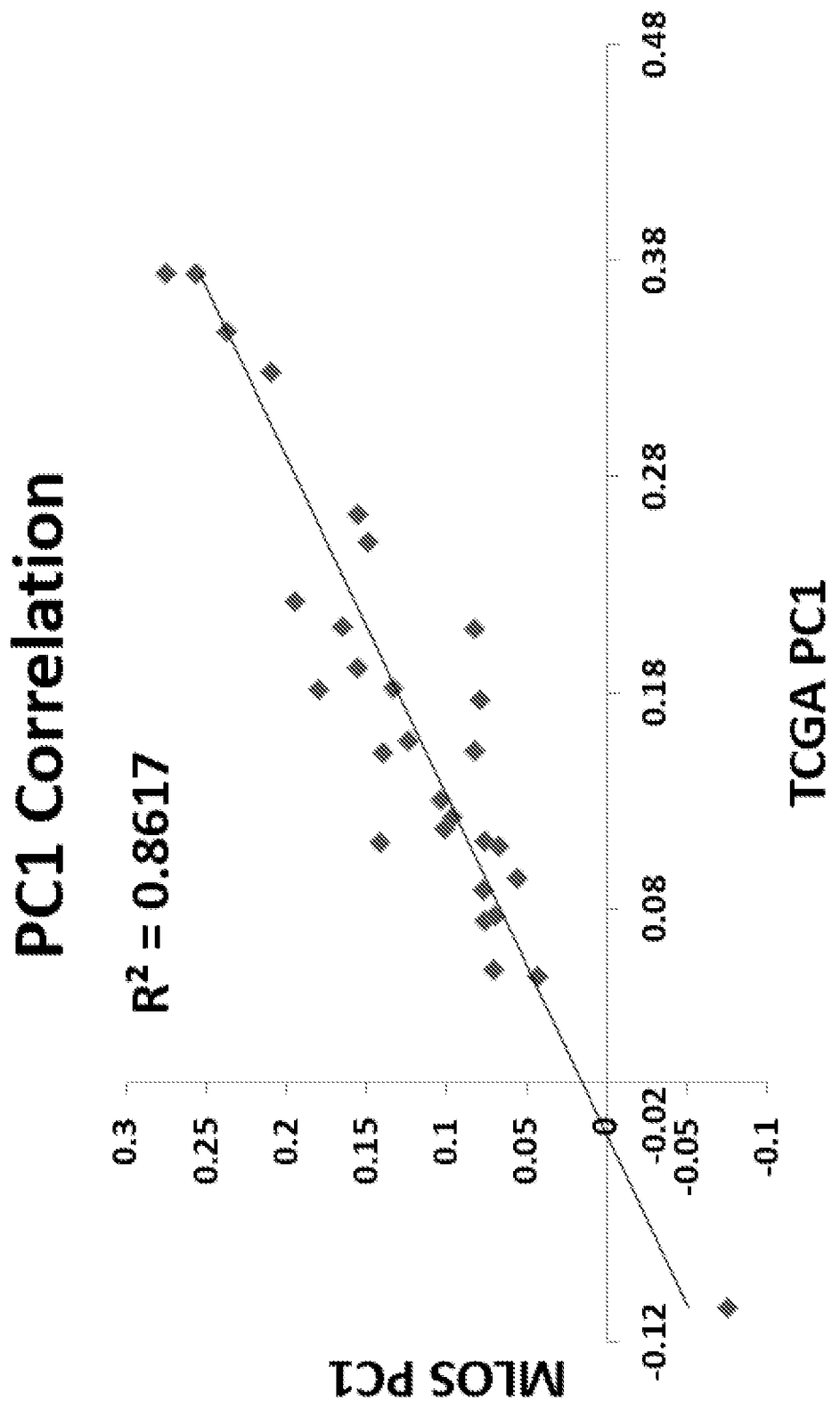
FIG. 6 is a Pearson Correlation of the first principal component of the MLOS and TOGA datasets using the 29 gene list.
Figure 7A:
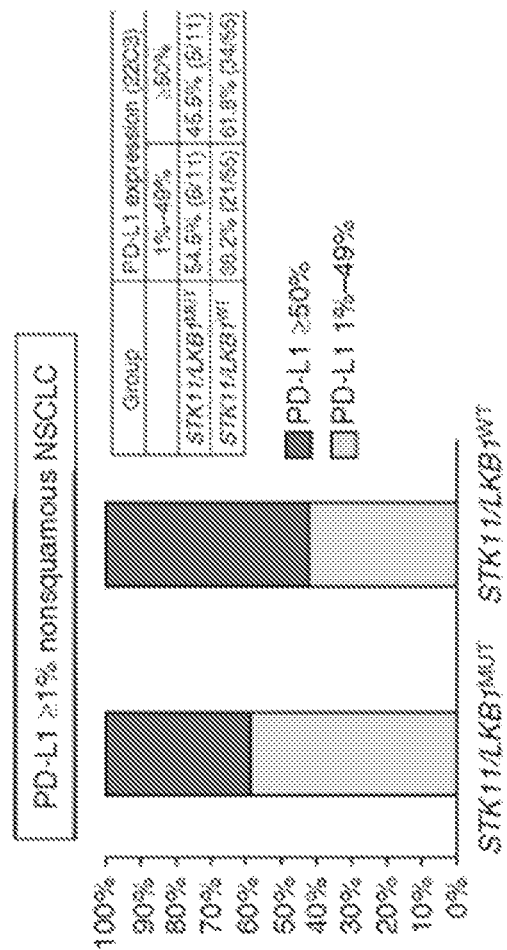
FIGS. 7A to 7D show STK11/LKB1 mutations are a genomic determinant of poor clinical outcome with PD-1 axis blockade in PD-L1-positive nonsquamous NSCLC, regardless of KRAS status.
Figure 7B:
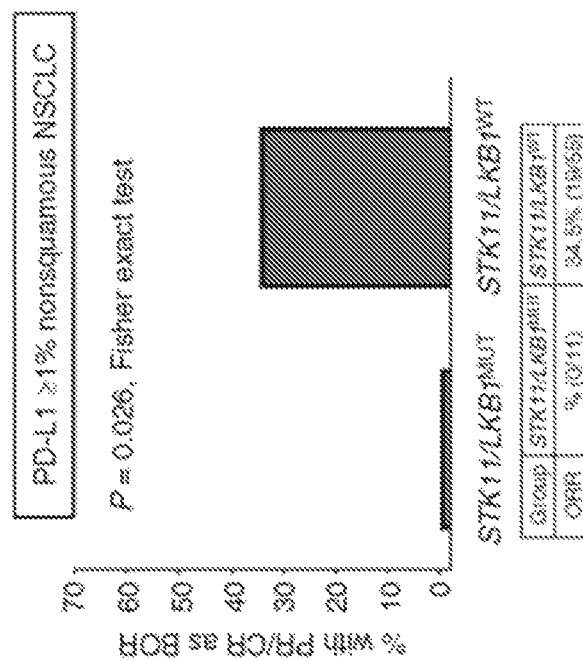
Figures 7C, 7D:
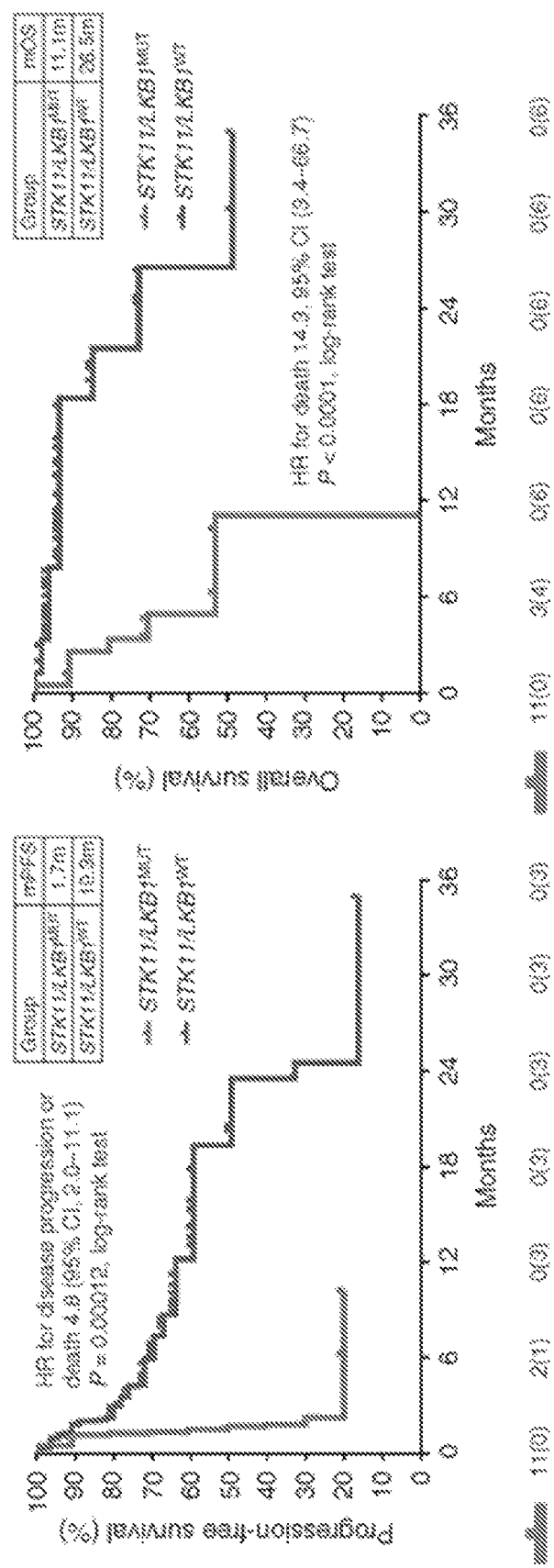

The strong relationship between Putrescine and GABA production in patients with predicted STK11 loss of function highlights the observed increase in amino acid catabolism through the deamination of putrescine. The increased level of vitamin B6 (pyridoxal) supports this observation. Pyridoxal is used as a co-factor when amino acids are utilized for energy through deamination or transamination reactions, in some cases both releasing ammonia and creating a carbon backbone. Evidence of this pathway is seen by the increase in gene expression of alanine aminotransferase (GPT2), ornithine aminotransferase (OAT), and histidine ammonia-lyase (HAL). Complementing these aminotransferase reactions is the increase in urea transport through SLC14A2 and key enzymes of the urea cycle, such as CPS1 and ODC1, suggesting the need to release an excess of ammonia. It was hypothesize that GABA could potentially be used as a TCA cycle intermediate through conversion to succinate as succinic acid is part of the putrescine-GABA co-expression network. (FIG. 5D).

Mummichog was then used to predict pathway and network analysis from m/z values in the metabolomics data. This software is capable of making multiple calls to indistinguishable m/z values, allowing for the statistical inference of metabolic pathways based on enrichment. When comparing untargeted metabolites between STK11 mutant and wildtype patients the most enriched pathway was arginine and proline metabolism (p=0.000945), both of which are precursors for the synthesis of ornithine required for polyamine metabolism. Other interesting pathways include fatty acid metabolism (p=0.001832) and the urea cycle (p=0.008426). Combined data from the transcriptome, proteome, and metabolome all converge to highlight the increase in amino acid catabolism, urea cycle, and polyamine metabolism in patients lacking functional STK11.

TABLE 6

Enriched pathways in predicted STK11 mutants through use of Mummichog

| Pathway | Overlap Size | Pathway Size | P-Value |
|---|---|---|---|
| Arginine and Proline Metabolism | 19 | 35 | 0.000945 |
| Carnitine shuttle | 13 | 21 | 0.000959 |
| Fatty acid activation | 9 | 17 | 0.001832 |
| Lysine metabolism | 12 | 27 | 0.002657 |
| Drug metabolism - other enzymes | 8 | 16 | 0.002891 |
| Aspartate and asparagine metabolism | 25 | 67 | 0.003461 |
| Tryptophan metabolism | 23 | 62 | 0.004141 |
| Glycerophospholipid metabolism | 17 | 44 | 0.004313 |
| Limonene and pinene degradation | 4 | 6 | 0.004526 |
| Beta-Alanine metabolism | 6 | 12 | 0.005374 |
| Vitamin B3 (nicotinate and nicotinamide) metabolism | 9 | 21 | 0.00567 |
| De novo fatty acid biosynthesis | 9 | 21 | 0.00567 |
| Valine, leucine and isoleucine degradation | 12 | 31 | 0.007426 |
| Urea cycle/amino group metabolism | 17 | 47 | 0.008426 |
| Butanoate metabolism | 9 | 23 | 0.011134 |
| Drug metabolism - cytochrome P450 | 15 | 43 | 0.014874 |
| Phytanic acid peroxisomal oxidation | 3 | 5 | 0.017027 |
| Nitrogen metabolism | 3 | 5 | 0.017027 |
| Vitamin H (biotin) metabolism | 3 | 5 | 0.017027 |
| Fatty acid oxidation, peroxisome | 2 | 2 | 0.020698 |
| Glycosphingolipid metabolism | 9 | 26 | 0.030471 |
| N-Glycan Degradation | 3 | 6 | 0.0338 |
| Fatty Acid Metabolism | 4 | 10 | 0.044489 |
| Aminosugars metabolism | 11 | 34 | 0.044714 |
| TCA cycle | 6 | 17 | 0.045223 |

Discussion

Disclosed herein is an in vivo signature for functional loss of STK11, useful in the classification of patients. The evidence provided has shown that patients with loss of STK11 have elevated levels of ODC1 both gene and protein leading to increased production of putrescine, the product of ODC1 activity. It has been established that ODC1 is a target of MYC (Partanen J I, et al. Proc Natl Acad Sci USA 2007 104(37):14694-9; Liang X, et al. Oncol Rep 2009 21(4): 925-31; Tsai L H, et al. Oncogene 2015 34(13):1641-9; Mo X, et al. Mol Pharmacol 2017 91(4):339-47) and previous literature has shown that STK11 is a repressor of MYC activity. Loss of STK11 may take the brakes off of MYC and could be the mechanism behind the observed increase in polyamine synthesis. Given the immunosuppressive nature of both MYC-driven cancers and polyamine synthesis, targeted inhibition of this pathway in combination with anti-PD-1/PD-L1 immunotherapy may increase survival in patients with loss of STK11 function. ODC1 is targetable through the FDA approved drug DFMO (Difluromethylornithine), which acts as an irreversible inhibitor of ODC1 (Loprinzi C L, et al. J Cell Biochem Suppl 1992 161:153-5; Raul F. Biochem Soc Trans 2007 35(Pt 2):353-5; Bassiri H, et al. Transl Pediatr 2015 4(3):226-38; Saulnier Sholler G L, et al. PLoS One 2015 10(5):e0127246). Until now, DFMO has not been considered a treatment strategy for lung cancer, as it is most commonly associated with MYC/MYCN driven diseases such as prostate cancer or neuroblastoma respectively (Bassiri H, et al. Transl Pediatr 2015 4(3):226-38; Saulnier Sholler G L, et al. PLoS One 2015 10(5): e0127246). Taking the above mentioned associations into consideration, STK11 mutant tumors not only overexpress the MYC target ODC1, but also inhibition of this pathway with DFMO could be used to partially reverse the immunosuppressive characteristics as well as result in metabolic disruption and growth arrest. Unique to this cell lineage however, polyamine synthesis is appears to be shunted through GABA production rather than downstream polyamines spermidine and spermine. In support of this observation, ornithine and urea transport is also transcriptionally upregulated in patients with loss of STK11 function through genes SLC7A2 and SLC14A2 respectively.

Loss of STK11 greatly impacts cell lineage (Zhang H, et al. Nat Commun 2017 8:14922). Very clearly, STK11 mutations are associated with both the neuroendocrine and adenocarcinoma lineage; a majority of STK11 mutant lung adenocarcinomas mimic the large cell neuroendocrine characteristics of co-occurring KRAS and KEAP1 mutations, MYCN amplification, and expression of ASCL1 (Rekhtman N, et al. Clin Cancer Res 2016 22(14):3618-29). Therefore, these two cell types may share common genetic machinery that sets the stage for a unique metabolic phenotype resulting from STK11 loss. These data suggest that this loss results in synthesis and accumulation of the neurotransmitter, GABA, and its precursor putrescine, which fits the neuroendocrine cell fate (McCann P P, et al. Neurochem Res 1979 4(4):437-47; de Mello M C, et al. Neurochem Int 1993 22(3):249-53; Sequerra E B, et al. Neuroscience 2007 146 (2):489-93). Additionally, NKX2-1 positive type II pneumocytes, which give rise to lung adenocarcinoma, contain the enzymes required for this conversion (Uhal B D, et al. Am J Physiol 1991 261(4 Suppl):110-7; Mason R J. Respirology 2006 11 Suppl:S12-5; Beers M F, et al. Am J Respir Cell Mol Biot 2017 57(1):18-2). Monoamine oxidase is required for the conversion of putrescine to GABA-aldehyde and ALDH3A2 is required for the conversion of GABA-aldehyde to GABA, both of which correlate with ODC1, putrescine, and GABA. GABA might be acting to depolarize immune cells along with the other immunosuppressive intermediates downstream of the polyamine pathway (Bhat R, et al. Proc Natl Acad Sci USA 2010 107(6):2580-5; Jin Z, et al. Amino Acids 2013 45(1):87-94; Bhandage A K, et al. EBioMedicine 2018 30:283-94). In addition, GABA may also be used as an energy substrate of the TCA cycle through GABA's conversion to succinate through GABA-amino transferase, limited by the enzyme GABAT (Ravasz D, et al. Neurochem Int 2017 109:41-53). Notably, pyridoxal (vitamin B6) is required as a co-factor for nearly every transamination or deamination reaction and even for decarboxylation. The increase in pyridoxal seen in this subset of patients only further supports this hypothesis. It is worth noting that the conversion of GABA to succinate bypasses two NAD+ to NADH steps of the TCA cycle, isocitrate to alpha-ketoglutarate and alpha-ketoglutarate to succinate. This observation could potentially guide to metabolic vulnerabilities in STK11 deficient patients.

A difficulty of this study is that the pathway of interest has been shown to be one of the most intricately regulated of all human pathways with transcriptional and translational half-lives in the range of 5-30 minutes (Bassiri H, et al. Trans) Pediatr 2015 4(3):226-38; Miller-Fleming L, et al. J Mol Biol 2015 427(21):3389-406; Lenis Y Y, et al. Zygote 2017:1-12; Hogarty M D, et al. Cancer Res 2008 68(23): 9735-45). Additionally, ODC1 and polyamine metabolism does not appear to be upregulated in any cell line database, syngeneic mouse model, or xenograft model as a result of STK11 loss. However, every patient dataset shows a significant upregulation. Given the specificity of ODC1 activity to patient tumors, this study could have captured metabolic alterations missed in other model systems. This patient specificity may be a result of cellular plasticity and differentiation due to STK11 loss in cells grown outside their natural environment. A number of other studies have alluded to STK11's role in cell fate (Zhang H, et al. Nat Commun 2017 8:14922; Mollaoglu G, et al. Immunity 2018 49(4): 764-79 e9). Likely, various environmental stimuli and cell of origin greatly impact this observation. When dealing with potent regulators of metabolism such as STK11, it is important to study the cells in a similar metabolic environment that would be present in patients. Xenograft models and tissue culture fail to recapitulate many variables that would be altered exclusively in the lung such as: glucose, amino acids, fatty acids, immune cells, oxygen concentration, pH, paracrine signaling from stromal tissue, and many more. While mouse models seem to be the answer to this question, gene expression patterns are vastly different in murine and human tumors. Since neuroendocrine cells and type II pneumocytes constitute such a small fraction of lung cells, deleting STK11 non-specifically in the lung results in a tumor of mixed histology with cell lineages pertinent to lung adenocarcinoma making up far less than 10% of the tumor.

Example 2: Targeting Ornithine Decarboxylase as an Immuno-Therapeutic Target in STK11 (LKB1) Pathway-Deficient Non-Small Cell Lung Cancer STK11 is the fourth-most frequently mutated gene in lung adenocarcinoma, with loss of function occurring in up to 30% of all cases. Despite the high frequency of loss, no targeted therapies for STK11-mutant lung cancers are available in the clinic. For this reason, improving the therapeutic options for these patients is a high priority. STK11 functions a serine-threonine kinase that controls the activity of 12 AMPK-like kinases, thereby controlling a complex metabolic and transcriptional network. Accumulating evidence suggests STK11 mutations have a strong suppressive effect on immune surveillance. Specifically STK11 mutations are associated with increased neutrophil infiltration and with reduced levels of intratumoral CD4+ and CD8+ T cells. Importantly, STK11-mutant tumors display a very poor and limited response to PD-1 blockade. For example, while 28.6% of lung adenocarcinoma patients having a KRAS mutation respond to PD-1 blockade, patients with both KRAS and STK11 mutations have an objective response rate of only 7.4%.

FIGS. 7A to 7D demonstrate the major differences in response rates to PD-1 therapy among PD-L1 >1% non-squamous NSCLC patients with and without STK11 mutations. Most importantly, FIG. 7D demonstrates that none of the STK11 mutant patients survives beyond one year of treatment, whereas median overall survival for STK11 wild type patients was over two years.

A cohort of well-characterized lung adenocarcinoma patients was studied, and the comprehensive genomic, transcriptomic, proteomic and metabolomic analyses revealed that the production of putrescine (and related metabolites) by ornithine decarboxylase (ODC1) may be a key metabolic driver of immune suppression. Difluoromethylornithine (DFMO, a.k.a. Eflornithine) is an ODC inhibitor that has established immune modulatory effects. Further, DFMO has been previously evaluated in a Phase 1 clinical trial at 4 dose levels and a recommended phase II dose of 6750 mg/m$^2$ PO in combination with celecoxib, cyclophosphamide and topotecan has been established for relapsed/refractory high risk neuroblastoma.

Example 3: Targeting ODC Therapeutically with DFMO can Restore Benefit of PD-1 Blockade to STK11-Mutant Patients without Toxicity To test whether targeting ODC therapeutically with DFMO will restore benefit of PD-1 blockade to STK11-mutant patients without toxicity, the following objects are explored: perform a Phase I dose escalation trial in STK11-mutant patients with DFMO in patients receiving standard of care pembrolizumab; perform Phase II trial of pembrolizumab+/−DFMO in two cohorts, and compare response rate to historical controls; and perform immunohistochemistry biomarker studies (TTF-1, c-Kit, PDL-1 and TIL markers) with both phases of the trial with pretreatment biopsies, on-treatment biopsies and a biopsy at progression to measure biomarkers.

One objective is to show that DFMO treatment in combination with Pembrolizumab is safe and tolerable. Another objective is to show that DFMO treatment increases response rate and progression-free survival in STK11-loss patients treated with Pembrolizumab. Another objective is to show that DFMO increases the number of tumor infiltrating lymphocytes in STK11-mutant tumors.

The purpose of the first study is to determine the recommended phase II dose of DMFO in the context of Pembrolizumab treatments, as follows: STK11 mutant (N=6-18 patients), immunotherapy naïve or pre-treated patients; dose escalation; and pembrolizumab, plus escalating DFMO.

Three different dose levels of DFMO PO Daily are used: Level 1: 4500 mg/m$^2$; Level 2: 6750 mg/m$^2$; Level 3: 9000 mg/m$^2$; and Level −1: 3000 mg/m$^2$, if applicable).

The purpose of the second study is to determine if addition of DMFO increases the response rate of STK11 mutant NSCLC patients to Pembrolizumab, as compared to historical controls, as follows.

Cohort A (N=36): Immunotherapy naïve patients. PD-L1, ≥1%*; Pembro & DFMO at the RP2D (as determined by dose escalation); baseline overall response rate 25% for comparison.

Cohort B (N=28): Immunotherapy pre-treated Patients. PD-L1, any*; Pembro, DFMO at the RP2D (as determined by dose escalation); baseline overall response rate 15% for comparison.

TABLE 7

Sample size (20% difference; n = 28-39*; statistical power = 80%; type I error = 5%)

| Study group | Response rate of historical data | Targeted response rate | r1 | n1 | r | n |
|---|---|---|---|---|---|---|
| Cohort A | 0.25 | 45% | 4 | 17 | 13 | 36 |
| Cohort B | 0.15 | 35% | 2 | 15 | 7 | 28 | r1: the maximum number of responders to reject drug in the first stage
n1: the sample size in the first stage
r: the maximum number of responders to reject drug at end of the study
n: the total sample size (combine both stages)

The schema above is powered to specifically test the hypothesis that DFMO improves progression free survival (PFS) in STK11 mutant patients by 20%. A faster and less costly study involves 20 patients per cohort, which can provide valuable information regarding a Go or No Go decision if the number of responding patients was greater than the number predicted from historical controls (5 in cohort A and 3 in cohort B).

Immunohistochemistry biomarker studies are performed on both phases of the trial with pretreatment biopsies, on-treatment biopsies, and a biopsy at progression, to measure expression of biomarkers, including TTF-1, c-Kit, PDL-1 and TIL markers.

Table 8 below is an example study calendar for Permbrolizumab plus DFMO:

TABLE 8

Study Calendar

| Trial Period Treatment Cycle/Title: | Study Screening (Visit 1) | Treatment Cycles | | | | | | | | | | To be repeated beyond 8 cycles | End of Treatment** Discon | Post-Treatment | | |
|---|---|---|---|---|---|---|---|---|---|---|---|---|---|---|---|---|
| | | 1 | 1 | 1 | 2 | 3 | 4 | 5 | 6 | 7 | 8 | | | Safety Follow-up | Follow up Visits | Survival Follow-up |
| Day: Scheduling Window (Days): | −27 to c1d1$^e$ | 1 | 8* ±4 | 15* ±7 | 1 ±7 | 1 ±7 | 1 ±7 | 1 ±7 | 1 ±7 | 1 ±7 | 1 ±7 | | At time of Discon ±7 | 30 days post end of treatment ±14 | Every 8 weeks post discon ±14 | Every 12 weeks ±14 |
| Screening Consent | X | | | | | | | | | | | | | | | |
| Informed Consent | X | | | | | | | | | | | | | | | |
| Inclusion/Exclusion Criteria | X | | | | | | | | | | | | | | | |
| Demographics and Medical History | X | | | | | | | | | | | | | | | |
| Prior and Concomitant Medication Review | X | X | X | X | X | X | X | X | X | X | X | | | | | |
| DFMO compliance review/Pill Diary | | X | X | X | X | X | X | X | X | X | X | | X | | | |
| Trial Treatment Administration | | X | X | X | X | X | X | X | X | X | X | | | | | |
| Post-study anticancer therapy status | | | | | | | | | | | | | X | X | | X |
| Survival Status | | X | X | X | X | X | X | X | X | X | X | | X | | | X |
| Review Adverse Events | X$^f$ | X | X | X | X | X | X | X | X | X | X | | X | X | | |
| Physical Examination | | X | X | X | X | X | X | X | X | X | X | | X | X | | |
| Vital Signs and Weight | X | X | X | X | X | X | X | X | X | X | X | | X | X | | |
| ECOG Performance Status | X | X | X | X | X | X | X | X | X | X | X | | | X | | |
| Pregnancy Test - Urine or Serum b-HCG | X | X | X | X | X | X | X | X | X | X | X | | | X | | |
| PT/INR and aPTT | X | | X | | | | | | | | | | | | | |
| CBC with Differential | X | X | X | X | X | X | X | X | X | X | X | | | X | | |
| Comprehensive Serum Chemistry Panel | X | X | X | X | X | X | X | X | X | X | X | | X | X | | |

TABLE 8-continued

Study Calendar

| Trial Period | Study | Treatment Cycles | | | | | | To be repeated | End of | Post-Treatment | | |
| --- | --- | --- | --- | --- | --- | --- | --- | --- | --- | --- | --- | --- |
| Treatment | Screening | | | | | | | beyond 8 cycles | Treatment** | Safety | Follow up | Survival |
| Cycle/Title: | (Visit 1) | 1 | 1 | 1 | 2 | 3 | 4 | 5 6 7 8 | Discon | Follow-up | Visits | Follow-up |
| Magnesium | X | X | | | X | X | X | X X X X | X | X | | |
| Urinalysis | X | | | | | | | | | | | |
| T3, FT4 and TSH | X | X | | | X | X | X | X X X X | X | X | | |
| EKG | X | | | | | | | | | | | |
| Tumor Imaging (CT Thorax/Abdomen) | X | | | | X | | X | X X | X | | X$^d$ | |
| Brain MRI or Brain CT | X | | | | | | | | | | | |
| Archival/Newly Obtained Tissue Collection$^{a,b}$ | X | | | | | | | | | | | |
| Correlative Studies Blood Collection$^c$ | X$^e$ | X$^e$ | | X$^e$ | X$^e$ | X$^e$ | | X$^e$ | | X$^e$ | | | |

*C1D8 and C1D15 only apply to phase 1 dose escalation.
** End of Treatment is defined as the date the decision was made to stop treatment.
$^a$All patients in the study are required to have a pre-treatment biopsy or archival tissue which will be tested for PD-L1 and LKB1.
$^b$C1D15-21 biopsies will be done on patients in all parts of the study for biomarker analysis.
$^c$The blood will be collected in five 10 mL green top (sodium heparin) tubes for a total of about 50 mL of whole blood. The correlative blood studies will occur on the same day as the biopsy where applicable.
$^d$Subjects who discontinue trial treatment for a reason other than disease progression or initiation of subsequent therapy will move into the Follow-Up Phase and should be assessed every 8 weeks (56 ± 7 days) by radiologic imaging to monitor disease status within year 1. After 1 year, the imaging time point will occur every 12 weeks (±7 days).
$^e$The main study screening window will occur within 28 days prior to the first study treatment. Note additionally that screening laboratory blood and urine studies must be obtained within 10 days of C1D1, with the exception of pregnancy testing in applicable patients, which must be obtained within 72 hours of first treatment.
$^f$Only serious adverse events will be collected during the screening window.

Example 4

Figure 8:
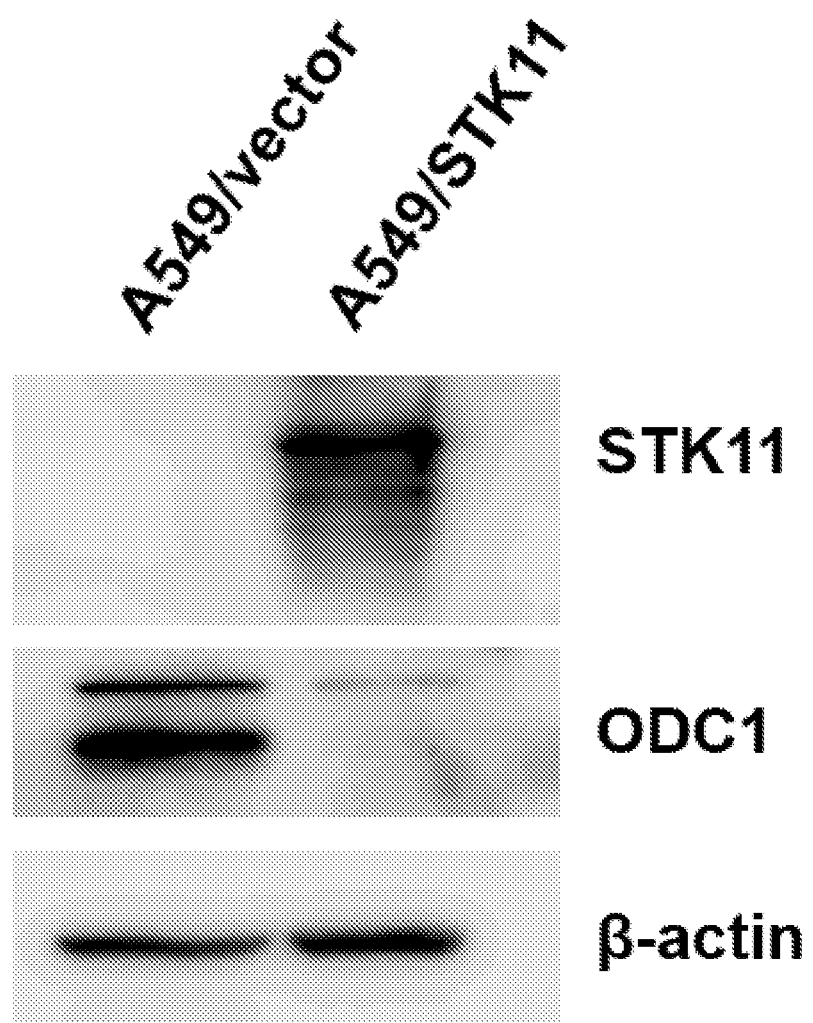
FIG. 8 shows reintroduction of functional STK11 silences the expression of ODC1 (compare A549/vector with A549/STK11).

The upregulation of ODC1 in STK11 mutant patients was not anticipated. To validate this observation functional STK11, we reintroduced into an STK11-deficient human cell line, A549 using a retroviral vector. The data in FIG. 8 demonstrates that reintroduction of functional STK11 silences the expression of ODC1 (compare A549/vector with A549/STK11), as predicted.

A549 cells (which are devoid of STK11 protein) were transduced with an empty retroviral vector (A549/vector) or with an STK11-expressing retrovirus (A549/STK11). Cells were seeded on day one at equal density and are harvested 96 hours later. Western blotting revealed that the STK11 retrovirus drives expression of the STK11 protein as evident in the top panel, labeled STK11. In the next panel, labeled ODC1, it is evident that STK11 expression silences ODC1 expression. The final panel labeled β-actin is a loading control.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating a subject with lung cancer, consisting of
   (a) assaying a biopsy sample comprising lung cancer cells from the subject for STK11 (Liver kinase 1, LKB1) somatic mutations, protein biomarkers of STK11 signaling, mRNA biomarkers of STK11 signaling, or any combination thereof;
   (b) detecting from the assay a loss of STK11 function in the lung cancer cells;
   (c) administering to the subject a therapeutically effective amount of an ornithine decarboxylase (ODC) inhibitor to treat the lung cancer;
   (d) administering to the subject an immunotherapy agent; and
   (e) optionally administering to the subject celecoxib, cyclophosphamide, topotecan, or any combination thereof.

2. The method of claim 1, wherein the ODC inhibitor comprises difluromethylornithine (DFMO), or a pharmaceutically acceptable salt thereof.

3. The method of claim 1, wherein the immunotherapy agent is a checkpoint inhibitor.

4. The method of claim 3, wherein the checkpoint inhibitor comprises an antibody that binds programmed cell death protein 1 (PD-1), an antibody that binds programmed death-ligand 1 (PD-L1), or a combination thereof.

5. The method of claim 2, comprising administering the DFMO at a dose of about 6750 mg/m$^2$.

6. The method of claim 1, wherein the protein biomarkers of STK11 signaling are selected from the group consisting of STK11, ODC1, TTF1 (transcription termination factor 1) and c-Kit (tyrosine-protein kinase KIT).

7. The method of claim 1, wherein the mRNA biomarkers of STK11 signaling are selected from the group consisting of CPS1 (carbamoyl-phosphate synthase 1), CALCA (calcitonin related polypeptide alpha), FGL1 (fibrinogen Like 1), LINC00473 (Long Intergenic Non-Protein Coding RNA 473), INSL4 (Insulin Like 4), INHA (Inhibin Subunit Alpha), SLC14A2 (solute carrier family 14 member 2), SLC7A2 (solute carrier family 7 member 2), SLC16A14

(solute carrier family 16 member 14), HAL (Histidine Ammonia-Lyase), PPARGC1A (PPARG coactivator 1 alpha), DUSP4 (dual specificity phosphatase 4), FXYD4 (FXYD Domain Containing Ion Transport Regulator 4), BMP6 (Bone Morphogenetic Protein 6), GLTPD2 (glycolipid transfer protein domain containing 2), GALNTL6 (N-acetylgalactosaminyltransferase like 6), KCNU1 (potassium calcium-activated channel subfamily U member 1), PDE3A (Phosphodiesterase 3A), PDE4D (Phosphodiesterase 4D), ODC1 (ornithine decarboxylase 1), IRS2 (insulin receptor substrate 2), EYS (Eyes Shut Homolog), TACC2 (transforming acidic coiled-coil containing protein 2), FURIN (Furin, Paired Basic Amino Acid Cleaving Enzyme), ADSSL1 (adenylosuccinate synthase 1), KSR1 (kinase suppressor of ras 1), VPS37A (Vacuolar protein sorting 37 homolog A), BAG1 (BAG cochaperone 1), and AIM1 (Absent in melanoma 1).

* * * * *